United States Patent
Schiff et al.

(10) Patent No.: US 8,150,523 B2
(45) Date of Patent: *Apr. 3, 2012

(54) FEEDBACK METHOD FOR DEEP BRAIN STIMULATION WITH DETECTION OF GENERALIZED EFFERENCE COPY SIGNALS

(75) Inventors: Nicholas D. Schiff, New York, NY (US); Keith Purpura, New York, NY (US); Steven Kalik, Arlington, MA (US)

(73) Assignee: Cornell Research Foundation, Inc., Ithaca, NY (US)

( * ) Notice: Subject to any disclaimer, the term of this patent is extended or adjusted under 35 U.S.C. 154(b) by 251 days.

This patent is subject to a terminal disclaimer.

(21) Appl. No.: 12/435,598

(22) Filed: May 5, 2009

(65) Prior Publication Data

US 2009/0216288 A1    Aug. 27, 2009

Related U.S. Application Data

(63) Continuation of application No. 10/320,840, filed on Dec. 16, 2002, now Pat. No. 7,539,543, which is a continuation of application No. 09/589,251, filed on Jun. 7, 2000, now Pat. No. 6,539,263.

(60) Provisional application No. 60/138,873, filed on Jun. 11, 1999.

(51) Int. Cl.
*A61N 1/36* (2006.01)

(52) U.S. Cl. .......................................... 607/45; 600/545

(58) Field of Classification Search .................... None
See application file for complete search history.

(56) References Cited

U.S. PATENT DOCUMENTS

| | | | |
|---|---|---|---|
| 4,014,323 A | 3/1977 | Gilmer et al. |
| 4,953,968 A | 9/1990 | Sherwin et al. |
| 5,052,401 A | 10/1991 | Sherwin |
| 5,170,780 A | 12/1992 | Rosenfeld |
| 5,269,303 A | 12/1993 | Wernicke et al. |
| 5,280,793 A | 1/1994 | Rosenfeld |
| 5,611,350 A | 3/1997 | John |
| 5,683,422 A | 11/1997 | Rise |
| 5,707,396 A | 1/1998 | Benabid |
| 5,716,377 A | 2/1998 | Rise et al. |

(Continued)

FOREIGN PATENT DOCUMENTS

EP    0 072 611 A1    2/1983

(Continued)

OTHER PUBLICATIONS

Barth et al., "Thalamic Modulation of High-Frequency Oscillating Potentials in Auditory Cortex," *Nature* 383:78-81 (1996).

(Continued)

*Primary Examiner* — Kennedy Schaetzle
(74) *Attorney, Agent, or Firm* — LeClairRyan, a Professional Corporation

(57) ABSTRACT

Disclosed is a method for improving cognitive function or for improving coordination of function across a patient's cortical regions. The method includes applying electrical stimulation to at least a portion of the patient's subcortical structures involved in the generation and control of generalized efference copy signals. Internally generated movement of the patient is then detected and, in response to such internally generated movement, application of electrical stimulation is controlled. The method of the present invention has a number of benefits, including increasing flexibility in identifying targets for stimulation, improving the probability of successfully treating brain injury, and permitting patient biofeedback and self-regulation.

38 Claims, 12 Drawing Sheets

U.S. PATENT DOCUMENTS

| | | | |
|---|---|---|---|
| 5,724,987 | A | 3/1998 | Gevins et al. |
| 5,752,979 | A | 5/1998 | Benabid |
| 5,792,186 | A | 8/1998 | Rise |
| 5,800,474 | A | 9/1998 | Benabid et al. |
| 5,833,709 | A | 11/1998 | Rise et al. |
| 5,843,148 | A | 12/1998 | Gijsbers et al. |
| 5,846,207 | A | 12/1998 | Rosenfeld |
| 5,938,688 | A | 8/1999 | Schiff |
| 6,016,449 | A | 1/2000 | Fischell et al. |
| 6,066,163 | A | 5/2000 | John |
| 6,104,956 | A | 8/2000 | Naritoku et al. |
| 6,161,045 | A | 12/2000 | Fischell et al. |
| 6,253,109 | B1 | 6/2001 | Gielen |
| 6,366,813 | B1 | 4/2002 | DiLorenzo |
| 6,463,328 | B1 | 10/2002 | John |
| 6,539,263 | B1 | 3/2003 | Schiff et al. |
| 7,539,543 | B2 | 5/2009 | Schiff et al. |
| 2009/0319001 | A1* | 12/2009 | Schiff ............................ 607/45 |

FOREIGN PATENT DOCUMENTS

| | | |
|---|---|---|
| EP | 0 585 303 B1 | 1/1997 |
| EP | 0 799 597 A1 | 10/1997 |
| EP | 0 832 667 A2 | 4/1998 |
| GB | 1 390 732 | 4/1975 |
| WO | WO 92/19172 | 11/1992 |
| WO | WO 94/00188 A1 | 1/1994 |
| WO | WO 95/05117 A1 | 2/1995 |
| WO | WO 97/45160 A1 | 12/1997 |

OTHER PUBLICATIONS

Benabid et al., "Chronic Electrical Stimulation of the Ventralis Intermedius Nucleus of the Thalamus as a Treatment of Movement Disorders," *J. Neurosurg.* 84:203-14 (1996).

Berg, "Screening Tests in Clinical Neuropsychology," Chapter 10, pp. 331-363, in Horton et al., eds., The Neuropsychology Handbook, vol. 1, Foundations and Assessment, 2nd ed., New York: Springer Publishing Company (1997).

Berson, "Cat Lateral Suprasylvian Cortex: Y-Cell Inputs and Corticotectal Projection," *J. Neurophysiology* 53(2):544-56 (1985).

Blakemore et al., "Why Can't You Tickle Yourself?," *NeuroReport* 11(113):R11-R16 (2000).

Bottini et al., "Modulation of Conscious Experience by Peripheral Sensory Stimuli," *Nature* 376:778-81 (1995).

Bridgeman, "A Review of the Role of Efference Copy in Sensory and Oculomotor Control Systems," *Annals of Biomedical Eng.* 23:409-22 (1995).

Bridgeman, "Efference Copy and its Limitations," *Computers in Biology and Med.* 37:924-9 (2007).

Cheu et al., "GABA Receptor Mediated Suppression of Defensive Rage Behavior Elicited from the Medial Hypothalamus of the Cat: Role of the Lateral Hypothalamus," *Brain Res.* 783:293-304 (1998).

Chronicle et al., "A Ticklish Question: Does Magnetic Stimulation of the Primary Motor Cortex Give Rise to an 'Efference Copy'?," *Cortex* 39:105-10 (2003).

Diedrichsen et al., "Anticipatory Adjustments in the Unloading Task: Is an Efference Copy Necessary for Learning?," *Exp. Brain Res.* 148:272-6 (2003).

Dossi et al., "Short-Lasting Nicotinic and Long-Lasting Muscarinic Depolarizing Responses of Thalamocortical Neurons to Stimulation of Mesopontine Cholinergic Nuclei," *J. Neurophysiology* 65(3):393-406 (1991).

Gainotti, "The Role of Spontaneous Eye Movements in Orienting Attention and in Unilateral Neglect," pp. 107-113, in Robertson et al., eds., Unilateral Neglect: Clinical and Experimental Studies, Hove, United Kingdom:Lawrence Erlbaum Associates, Publishers (1993).

Grunwerg et al., "Sensory Responses of Intralaminar Thalamic Neurons Activated by the Superior Colliculus," *Exp. Brain Res.* 88:541-50 (1992).

Hack, "Why Can't You Tickle Yourself?," *Moving* 6:211-215.

Heath, "Brain Function in Epilepsy: Midbrain, Medullary, and Cerebellar Interaction with the Rostral Forebrain," *J. Neurology, Neurosurgery, and Psychiatry* 39:1037-51 (1976).

Hinman et al., "Depth Evoked Potential and Single Unit Correlates of Vertex Midlatency Auditory Evoked Responses," *Brain Res.* 264:57-67 (1983).

Infante et al., "Electrophysiological Projections of Pulvinar-Lateralis Posterior Complex (P-LP) Upon Superior Colliculus Units in the Cat," *Archives Italiennes de Biobgie* 124:73-81 (1986).

Katayama et al., "Characterization and Modification of Brain Activity with Deep Brain Stimulation in Patients in a Persistent Vegetative State: Pain-Related Late Positive Component of Cerebral Evoked Potential," *Pace* 14:116-21 (1991).

Kinomura et al., "Activation by Attention of the Human Reticular Formation and Thalamic Intralaminar Nuclei," *Science* 271:512-5(1996).

Lo et al., "Control of Recurrent Inhibition of the Lateral Geniculate Nucleus by Afferents from the Superior Colliculus of the Rabbit: A Possible Mechanism of Saccadic Suppression," *Exp. Brain Res.* 68(2):421-7 (1987).

Lo, "A Study of Neuronal Circuitry Mediating the Saccadic Suppression in the Rabbit," *Exp. Brain Res.* 71(3):618-22 (1988).

Mantyh, "Connections of Midbrain Periaqueductal Gray in the Monkey. I. Ascending Efferent Projections," *J. Neurophysiology* 49(3):567-81 (1983).

Mennemeier et al., "Tapping, Talking and the Thalamus: Possible Influence of the Intralaminar Nuclei on Basal Ganglia Function," *Neuropsychologia* 35(2):183-93 (1997).

Noda et al., "Saccadic Eye Movements Evoked by Microstimulation of the Fastigial Nucleus of Macaque Monkeys," *J. Neuropysiology* 60(3):1036-52 (1988).

Pfaff et al., "Generalized Arousal of Mammalian Central Nervous System," *J. Comp. Neurology* 493:86-91 (2005).

Plum et al., "Coordinated Expression in Chronically Unconscious Persons," *Phil. Trans. R. Soc. Lond.* B 353:1929-33 (1998).

Posner, "Attention: The Mechanisms of Consciousness," *Proc. Natl. Acad. Sci. USA* 91:7398-403 (1994).

Purpura et al., "The Thalamic Intralaminar Nuclei: A Role in Visual Awareness," *Neuroscientist* 3(1):8-15 (1997).

Rinaldi et al., "Cognitive Effects of Left Medial Thalamic Stimulation in Two Patients with Deep Brain Electrodes for Relief of Chronic Pain," *Soc'y Neuroscience* 22:356.5 (1996) (abstract only).

Sayette et al., "Infarction in the Territory of the Right Choroidal Artery and Minor Hemisphere Syndrome: Case Report and Brain Glucose Utilisation Study," *Rev. Neurol.* (Paris) 151:24-35 (1995).

Schiff et al., "Cortical Function in the Persistent Vegetative State," *Trends Cognitive Sci.* 3(2):43-6 (1999).

Schiff et al., "Does Vestibular Stimulation Activate Thalamocortical Mechanisms that Reintegrate Impaired Cortical Regions?," *Proc. R. Soc. Lond.* B 266:421-3 (1999).

Schlag-Rey et al., "Visuomotor Functions of Central Thalamus in Monkey. I. Unit Activity Related to Spontaneous Eye Movements," *J. Neurophysiology* 51(6):1149-74 (1984).

Segraves et al., "Functional Properties of Corticotectal Neurons in the Monkey's Frontal Eye Field," *J. Neurophysiology* 58(6):1387-1419 (1987).

Shapalova et al., "Role of the Activation of the Intralaminar Nuclei of the Thalamus in Regulating the Participation of the Neostraital Cholinergic System in the Differentiation of Acoustic Signals in Dogs," *Neuroscience and Behav. Physiology* 25 (6):504-7 (1995).

Shiroyama et al., "Projections of the Vestibular Nuclei to the Thalamus in the Rat: A *Phaseolus vulgaris* Leucoagglutinin Study," *J. Comp. Neurology* 407:318-32 (1999).

Sinnamon et al., "Locomotion and Head Scanning Initiated by Hypothalamic Stimulation Are Inversely Related," *Behav. Brain Res.* 99:219-29 (1999).

Stanton et al, "Frontal Eye Field Efferents in the Macaque Monkey: II. Topography of Terminal Fields in Midbrain and Pons," *J. Comp. Neurology* 271:493-506 (1988).

Steriade, "Awakening the Brain," *Nature* 383: 24-5 (1996).

Tasker et al., "The Role of the Thalamus in Functional Neurosurgery," *Functional Neurosurgery* 6(1):73-104 (1995).

Vallar et al., "Modulation of the Neglect Syndrome by Sensory Stimulation," pp. 555-578, in Thier et al., eds., Parietal Lobe Contributions to Orientation in 3D Space, Heidelberg, Germany:Springer-Verlag (1997).

Velasco et al., "Electrocortical and Behavioral Responses Produced by Acute Electrical Stimulation of the Human Centromedian Thalamic Nucleus," *Electroencephalography and Clinical Neurophysiology* 102:461-71 (1996).

Velasco et al., "Neglect Induced by Thalamotomy in Humans: A Quantitative Appraisal of the Sensory and Motor Deficits," *Neurosurgery* 19(5):744-51 (1986).

Velasco et al., "Effect of Chronic Electrical Stimulation of the Centromedian Thalamic Nuclei on Various Intractable Seizure Patterns: II. Psychological Performance and Background EEG Activity," *Epilepsia* 34(6):1065-73 (1993).

Zhu et al., "Time Course of Inhibition Induced by a Putative Saccadic Suppression Circuit in the Dorsal Lateral Geniculate Nucleus of the Rabbit," *Brain Res. Bull.* 41(5):281-91 (1996).

International Search Report for PCT/US98/21935 (Jan. 29, 1999).

Decision of the Technical Board of Appeal 3.4.01 of Mar. 30, 2011, for European Patent Application No. 98953638.8 (mailed May 20, 2011).

Communication of the Board of Appeal for European Patent Application No. 98953638.8 (Sep. 9, 2010).

Decision of the Examining Division regarding European Patent Application No. 98953638.8 (Oct. 15, 2007).

Communication Under Rule 51(4) EPC regarding European Patent Application No. 98953638.8 (Apr. 20, 2007).

Result of Consultation for European Patent Application No. 98953638.8 (Dec. 22, 2006).

Summons to Attend Oral Proceedings regarding European Patent Application No. 98953638.8 (Sep. 27, 2006).

International Search Report for PCT/US00/15798 (Sep. 21, 2000).

International Preliminary Examination Report for PCT/US00/15798 (Jun. 15, 2001).

Communication Pursuant to Article 96(2) EPC for European Patent Application No. 00939701.9-2305 (Apr. 5, 2004).

Decision of the Technical Board of Appeal 3.4.01 of Mar. 31, 2011, for European Patent Application No. 05075990.1 (mailed Jun. 30, 2011).

Communication of the Board of Appeal for European Patent Application No. 05075990.1 (Nov. 29, 2010).

Decision of the Examining Division regarding European Patent Application No. 05075990.1 (Jan. 24, 2008).

Summons to Attend Oral Proceedings regarding European Patent Application No. 05075990.1 (Aug. 23, 2007).

Communication Pursuant to Article 96(2) EPC for European Patent Application No. 05075990.1 (Mar. 13, 2006).

European Search Report for European Patent Application No. 05075990.1, Jun. 9, 2005 (mailed Jun. 21, 2005).

Blouin et al., "Encoding Target-Trunk Relative Position: Cervical Versus Vestibular Contribution," Exp. Brain Res., 122(1): 101-7 (1998).

Evarts and Fromm, "Transcortical Reflexes and Servo Control of Movement," Can. J. Physiol. Pharmacol., 59(7): 757-75 (1981).

Gallistel, C.R., The Organization of Action: A New Synthesis 166-209 (Lawrence Erlbaum Assoc. (1980)).

Jones, E.G., "Viewpoint: The Core and Matrix of Thalamic Organization," Neuroscience, 85(2): 331-45 (1988).

Robertson et al., "Prospects for the Rehabilitation of Unilateral Neglect," in Robertson et al., Unilateral Neglect: Clinical and Experimental Studies, Psychology Press (1993).

Taube and Muller, "Comparisons of Head Direction Cell Activity in the Postsubiculum and Anterior Thalamus of Freely Moving Rats," Hippocampus, 8(2): 87-108 (1988).

Canadian Intellectual Property Office Official Action regarding Canadian Patent Application No. 2,306,821 (May 1, 2009).

* cited by examiner

FEEDBACK METHOD FOR DEEP BRAIN STIMULATION WITH DETECTION OF GENERALIZED EFFERENCE COPY SIGNALS

This application is a continuation of U.S. patent application Ser. No. 10/320,840, filed Dec. 16, 2002, now U.S. Pat. No. 7,539,543, issued May 26, 2009, which is a continuation of U.S. patent application Ser. No. 09/589,251, filed Jun. 7, 2000, now U.S. Pat. No. 6,539,263, issued Mar. 25, 2003, which claims the benefit of U.S. Provisional Patent Application Ser. No. 60/138,873, filed Jun. 11, 1999.

The invention was made with government support under Grant Nos. NS36699 and KO8 NS02014-02 awarded by National Institutes of Health. The U.S. Government has certain rights.

FIELD OF THE INVENTION

The present invention relates generally to a feedback mechanism for deep brain electrical stimulation methods and, more particularly, methods for treating conscious patients having impaired cognitive function.

BACKGROUND OF THE INVENTION

Brain injuries which lead to impaired cognitive function remain the least explored area for active neurological intervention. Several clinical observations suggest that mechanisms of plasticity are available to the brain that might be harnessed for therapeutic advantage for treating cognitive disorders. A significant percentage, roughly 20%, of patients who suffer severe brain damage remain conscious with preserved capacity for memory, attention, intention, and awareness. In many cases, these patients fluctuate dramatically (e.g., the well-known case of Gary Dockery, the brain-injured police officer who "woke up" and interacted with his family for nearly twenty-four hours after seven years of minimal responsiveness—Chicago Tribune Jan. 29, 1997 "After Miracle Coma Patient Has Way to Go").

There has been a striking lack of therapeutic options for these patients, despite evidence of their capacity to further optimize their brain function; this capacity is evident in the spontaneous fluctuations of functional level in many patients and the induced functional changes in some patients following sensory stimulation or patient initiated behaviors. The significance of developing a therapeutic intervention for patients having impaired cognitive function, especially those who remain conscious with preserved capacity for memory, attention, intention, and awareness lies in both the devastating reduction in quality of life they suffer and the economic burden these patients place on the health care system. These costs include full-time care in nursing and chronic rehabilitation facilities. Moreover, head trauma accounts for the largest percentage of these patients and most patients having impaired function caused by head trauma are under 40 years of age. Such patients represent a disproportionate economic cost in terms of both the loss of their expected productivity and the attendant costs of very long-term full-time care based on their young age.

Vestibular stimulation has been shown to reverse cognitive impairments. Schiff, et al., "Does Vestibular Stimulation Activate Thalamocortical Mechanisms That Reintegrate Impaired Cortical Regions?," *Proc. R. Soc. Land. B.* 266:421-23 (1999). However, improved procedures for controlling such stimulation is needed.

The present invention is directed to overcoming this deficiency.

SUMMARY OF THE INVENTION

The present invention relates to a method for treating a conscious patient to improve cognitive function. The method includes selecting a conscious patient who may or may not have impaired cognitive function. Electrical stimulation is then applied to at least a portion of the patient's subcortical structures involved in the generation and control of generalized efference copy signals under conditions effective to improve the patient's cognitive function. Internally generated movement of the patient is then detected and, in response to such internally generated movement, application of electrical stimulation is controlled.

The present invention also relates to a method for improving coordination of function across cortical regions in a patient. The method includes applying electrical stimulation to two or more subdivisions of the subcortical structures integrated in the generation and control of generalized efference copy signals. The two or more subdivisions modulate separate cortical regions. Electrical stimulation is again followed by detection of internally generated movement of the patient and, in response, control of the electric stimulation.

Using the methods of the present invention, patients suffering from impaired cognitive function can have at least a portion of the function restored, thus improving their quality of life and reducing societal costs. As a method of deep brain stimulation the present invention has several specific advantages over empirical adjustment of frequency and intensity of the electrical stimulation alone by identifying a natural pulse sequence for patterning of the stimulation. The added utility of these feedback pulses is that they offer increased flexibility in terms of both identifying additional targets of stimulation by using a synchronizing pulse that these areas are prepared to receive and improving the probability that complex brain injuries may be successfully treated because of a greater selectivity of using a natural pulse sequence. An important additional therapeutic advantage is that feedback as used here allows for patient biofeedback and self-regulation to play a role in the use of the application of the simulation technology for therapeutic purposes.

DETAILED DESCRIPTION OF THE INVENTION

Figure 1:
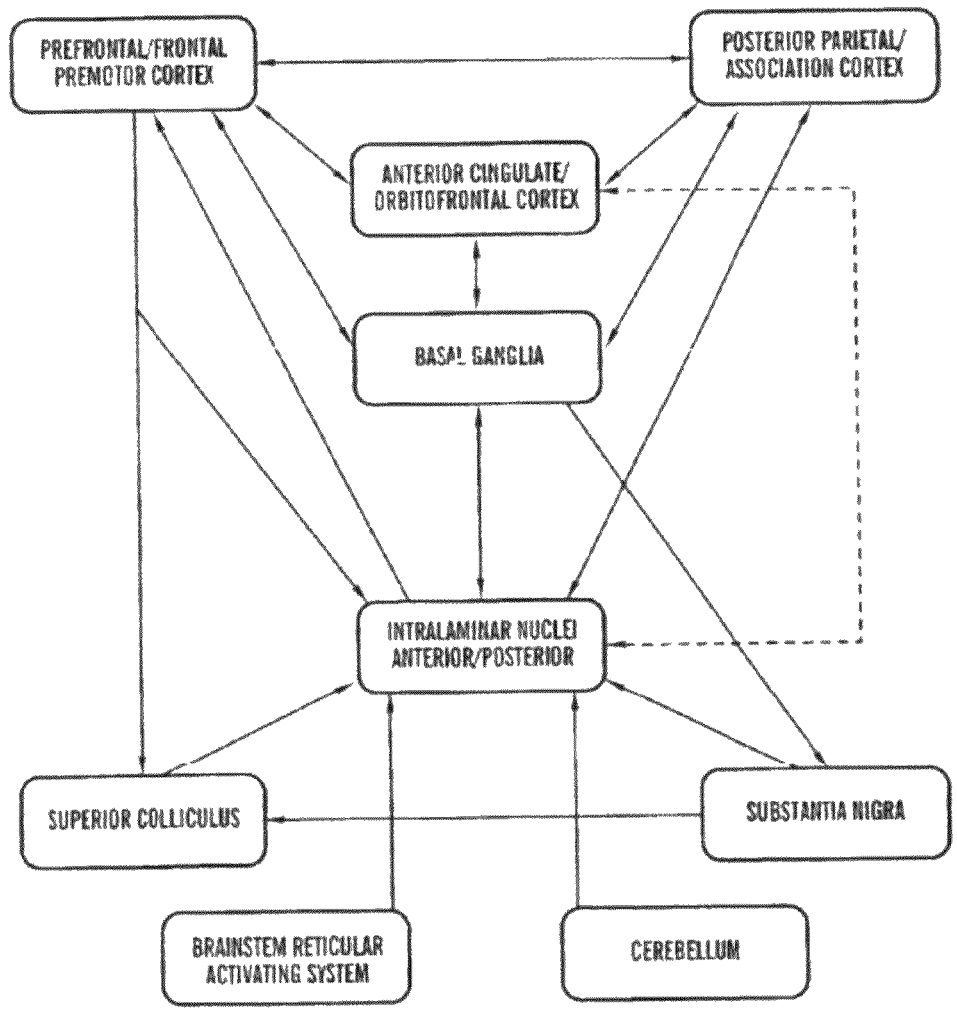
FIG. 1 is a schematic diagram of the anatomical connections of the intralaminar nuclei with distributed circuits underlying arousal, attention, and gaze control.
Figure 2A:
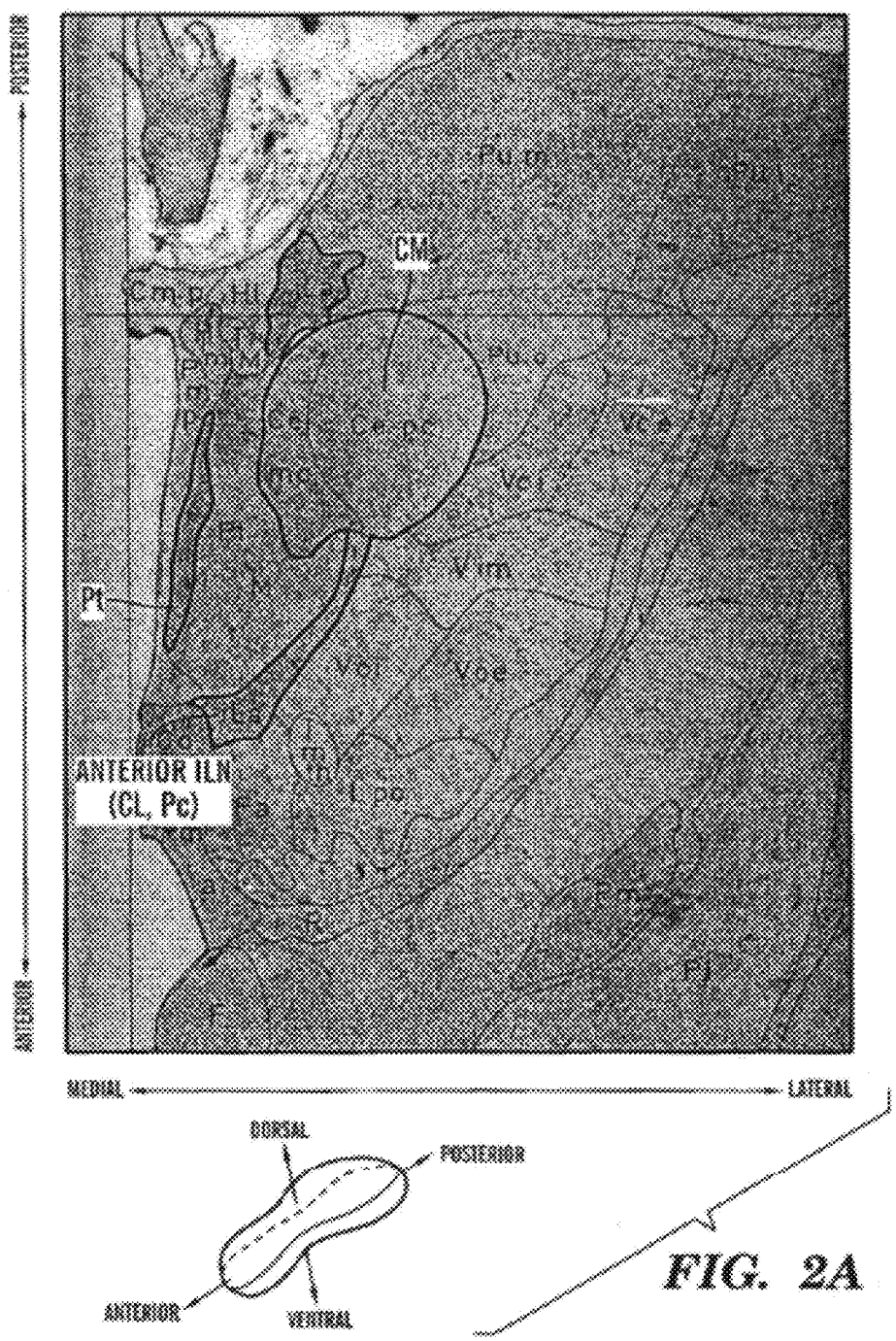
FIGS. 2A-2E are photographs of brain sections illustrating intralaminar nuclei subdivisions suitable for stimulation in accordance with the practice of the present invention.
Figure 2B:
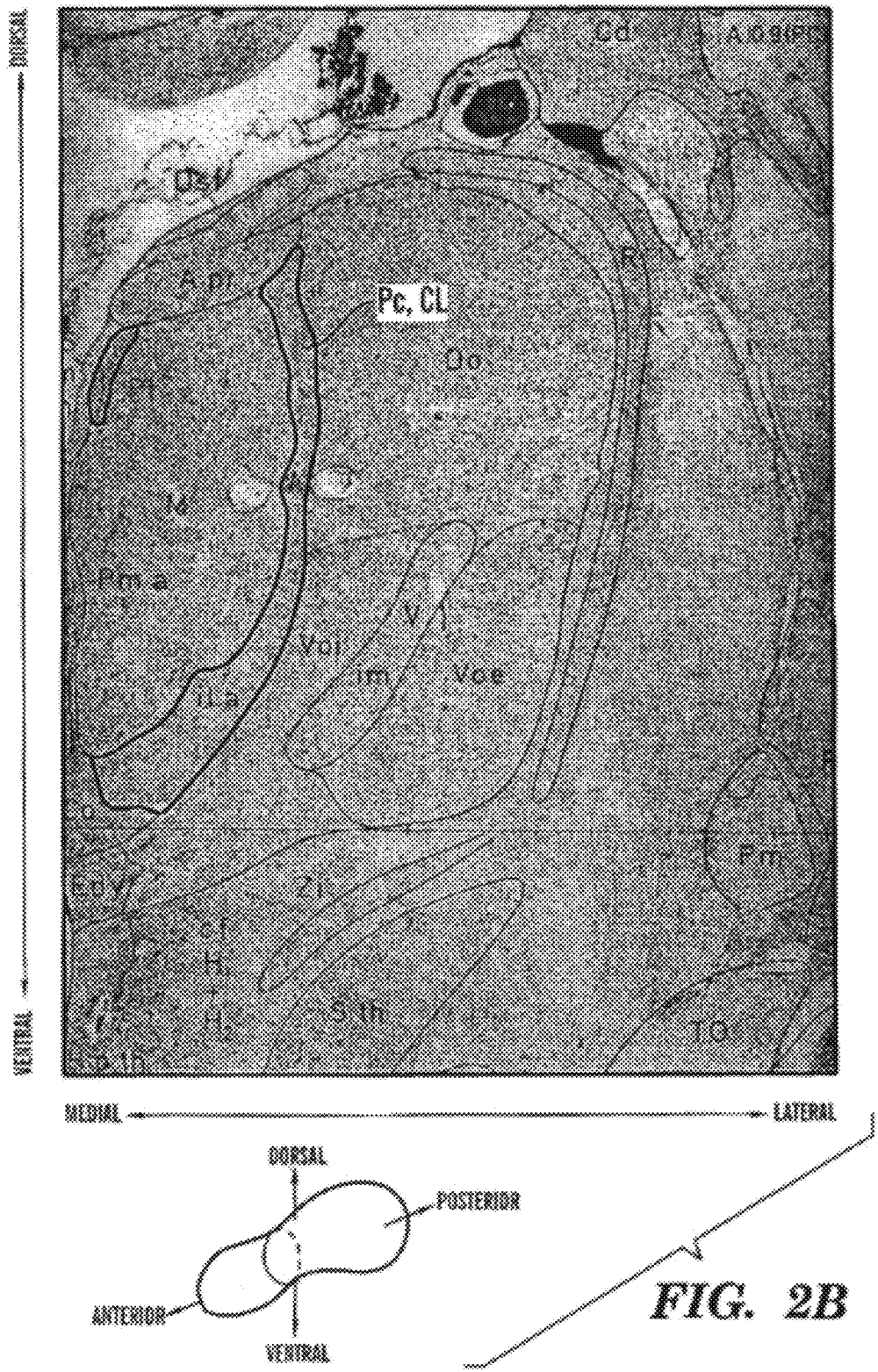
Figure 2C:
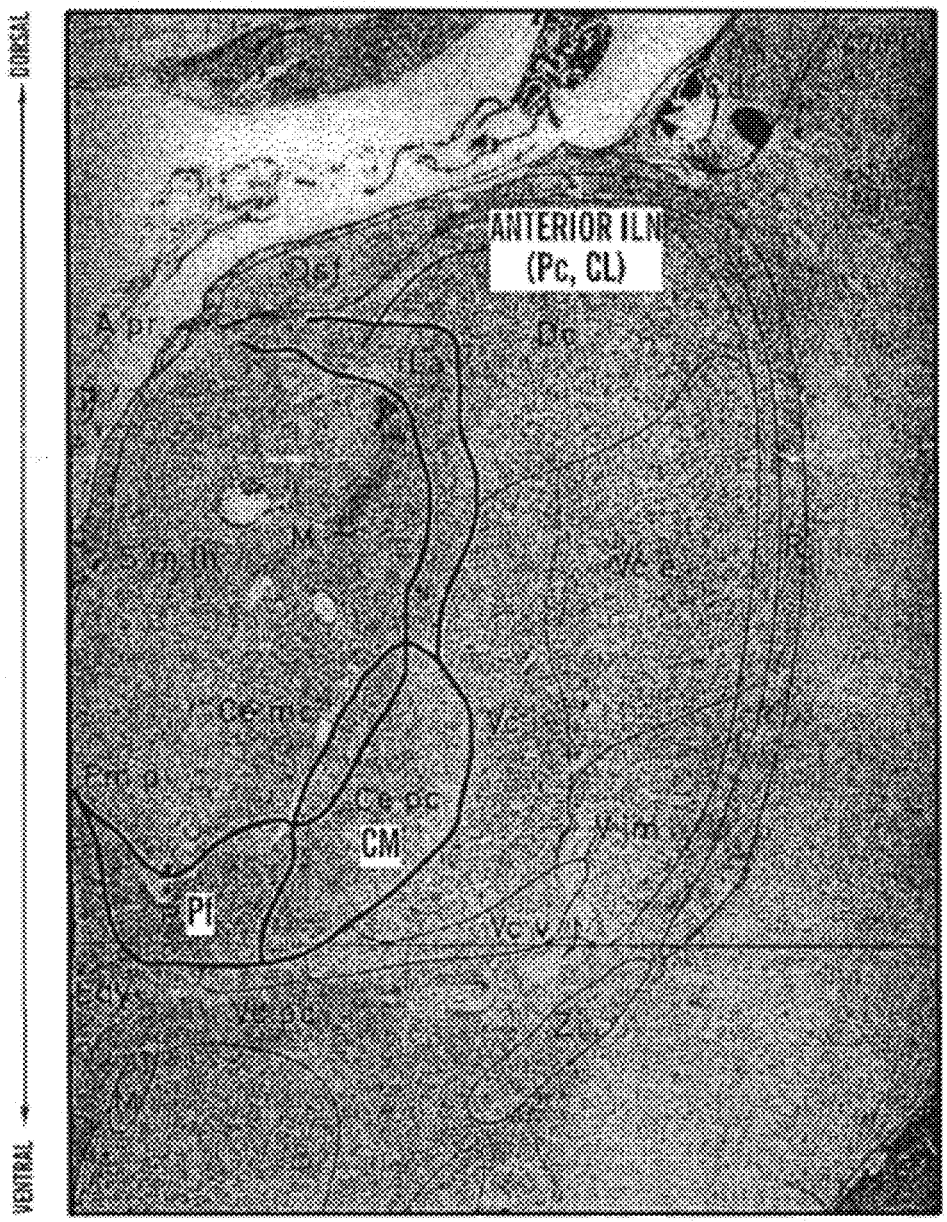
Figure 2C:
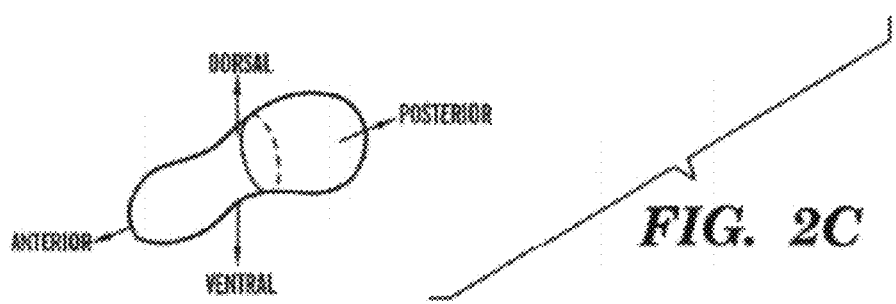
Figure 2D:
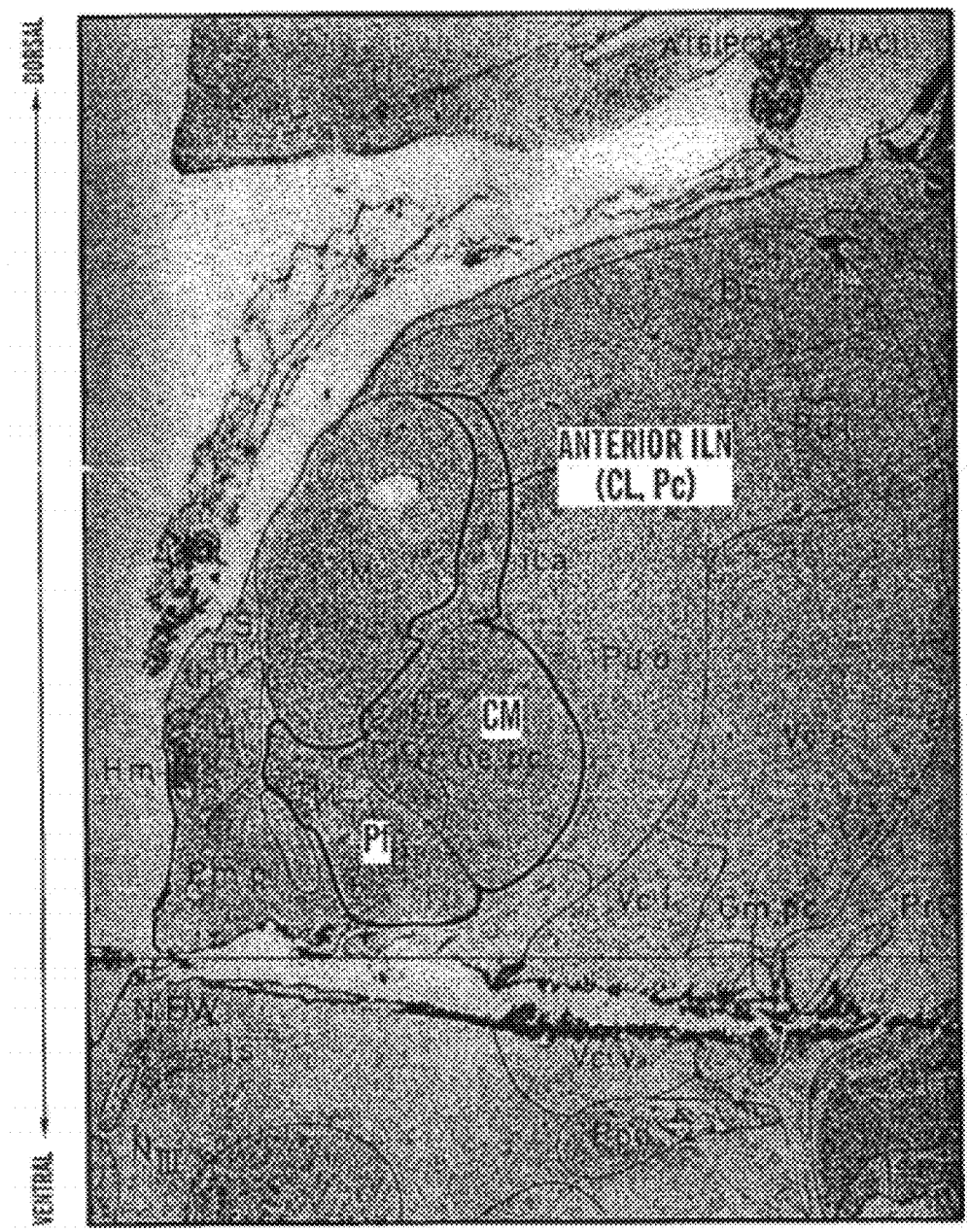
Figure 2D:
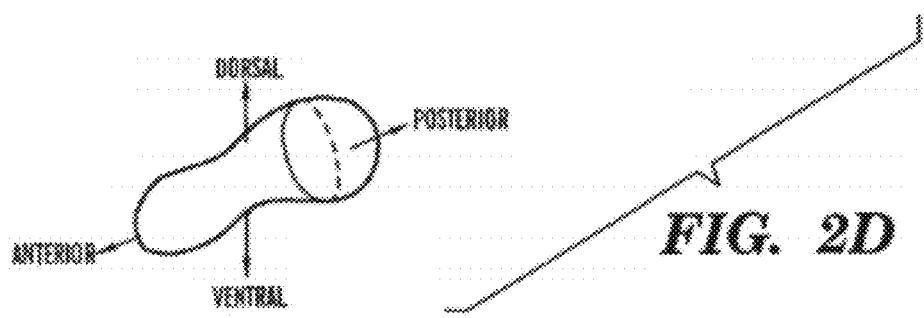
Figure 2E:
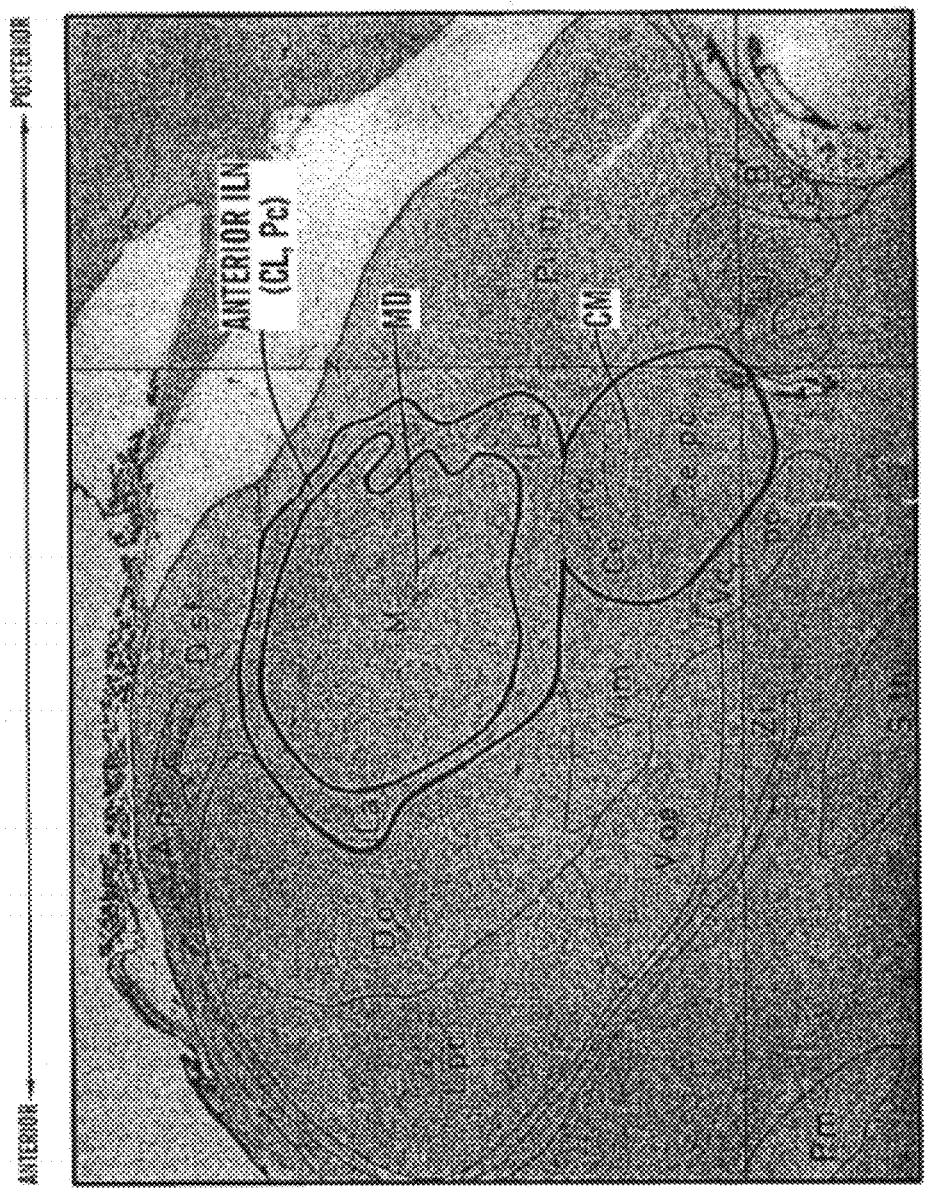
Figure 2E:
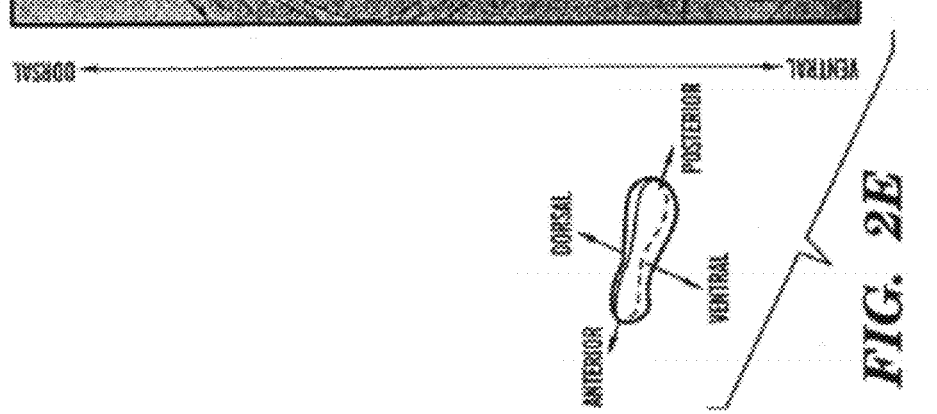

The present invention relates to a method for treating a conscious patient to improve cognitive function. The method includes selecting a conscious patient who may or may not have impaired cognitive function. Electrical stimulation is then applied to at least a portion of the patient's subcortical structures involved in the generation and control of generalized efference copy signals under conditions effective to improve the patient's cognitive function. Internally generated movement of the patient is then detected and, in response to such internally generated movement, application of electrical stimulation is controlled.

As used herein, cognitive function means the information processing capacities of the brain, including all semantic information processing, including interpretation of external and internal sensory signals and integration of those signals to support behavior. Perceptual awareness, as used herein, is a subset of cognitive function and is meant to include the mechanisms of selecting, organizing, and classifying internally or externally generated brain signals. A variety of methods can be used to assess a patient's cognitive function and to detect deficits in perceptual awareness. These include clinical neurological and neuropsychological evaluation and administration of detailed neuropsychological test batteries.

The patient with impaired cognitive function may have that condition alone, or, alternatively, the patient may suffer from a variety of other ailments in addition to impaired cognitive function. Such other ailments may include chronic pain or generalized seizures, each of which conditions may be present without the other. Alternatively, patients with impaired cognitive function may additionally suffer from both chronic pain and generalized seizures. Patients with impaired cognitive function alone, patients with impaired cognitive function accompanied by either chronic pain or generalized seizures, and patients with impaired cognitive function accompanied by both chronic pain and generalized seizures can all benefit from the practice of the present invention. As used herein, chronic pain means a syndrome of protracted pain, typically resulting from a persistent activation of central pain mechanisms (i.e., in the brain (commonly referred to as "neuropathic pain") as opposed to pain which results primarily from activation of pain mechanisms in the peripheral nervous system. As used herein, generalized seizures is meant to include epileptic seizures, such as those experienced by severe medication resistant refractory epileptics (i.e., patients who have been treated with multiple anti-epileptic medications at near toxic doses and failed this therapy as evidenced by their continuing to have multiple seizures daily despite such medication).

The method of the present invention can be practiced on patients whose cognitive dysfunction (e.g., impaired perceptual awareness) is, for example, produced, at least in part, by brain injuries, including those produced, at least in part, by stroke, head trauma (e.g., blunt head trauma or missile penetration), toxicological agents (e.g., carbon monoxide, arsenic, or thallium), anoxia (e.g., reduced oxygen levels in the blood), ischemia (e.g., reduced blood flow), nutritional deficiencies, developmental diseases, infectious diseases, neoplastic diseases, degenerative diseases, complications thereof, or other structural lesions.

These brain injuries frequently manifest themselves in combined deficits of attention, intention, working memory, and/or awareness. As used herein, attention refers to the cognitive function that provides the capacities for selection of internal or external stimuli and thoughts, supports the preparation of intended behaviors (e.g., speeds perceptual judgments and reaction times), and supports the maintenance of sustained cognition or motor behaviors (e.g., the focusing of attention). Intention, as used herein, refers to the mechanism of response failures (i.e., lack of behavioral interaction) which is not due to a perceptual loss (i.e., intention is the cognitive drive linking sensory-motor integration to behavior). Intention deficits include failure to move a body part despite intact motor pathways, awareness, and sensory processing as demonstrated by neurophysiological and neuropsychological evaluation. Another example of a patient's intention deficit is a failure to initiate action of any kind despite evidence of awareness or action produced by stimulation. Loss of intention is a disorder of cognitive function, as defined herein, and is a major division of the neuropsychological disorder of neglect, which may be present in many patients with cognitive loss following brain injury. Working memory, as used herein, refers to the fast memory process required for on-line storage and retrieval of information, including processes of holding incoming information in short-term memory before it can be converted into long-term memory and processes which support the retrieval of established long-term (episodic) memories. Deficits in awareness relate to impaired perceptual awareness, as described above. Clinical signs of these brain injuries also include profound hemi-spatial neglect, disorders of motor intention, disorders of impaired awareness of behavioral control, or apathy and cognitive slowing.

A patient's attention, intention, working memory, and/or awareness function can be evaluated using standard tests. Most of these test batteries encompass the different types of basic cognitive functions and are used to initially screen a patient for a pattern of deficits. More specific tests can be employed and individualized to a patient's neuropsychological profile. In practice, the choice of particular neuropsychological test batteries depends on the experience of the tester and the normative data available for the test. This changes as new studies are done and as new testing materials are tried out and compared. For example, suitable comprehensive tests include the Mental Status Exam ("MSE") (set forth, for example, in Strub et al., *The Mental Status Exam in Neurology*, 3rd ed., Philadelphia:Davis (1993), which is hereby incorporated by reference) as well as broad neuropsychological test batteries, like the Halstead-Reitan Neuropsychological Test Battery (which encompasses memory, attention, intention, and perception/awareness). In order to delineate more narrowly specific deficits of working memory, attention, perception, etc., more individualized tests can be chosen. For example, a 'Shipley-Hartford scale' test may be employed to assess cognitive slowing (intelligence); a 'Bender-Gestalt' test can be used to assess spatial relations and constructions; Aphasia screening tests, such as the Boston Diagnostic Aphasia Examination or the Western Aphasia Battery, can detect language dysfunction; and Trials A/B or Memory Assessment Scales ("MAS") test can be used to assess working memory. Further details with regard to these and other tests for assessing a patient's attention, intention, working memory, and/or awareness function can be found in, for example, Berg, "Screening Tests in Clinical Neuropsychology," Chapter 10, pp. 331-363, in Horton et al., eds., *The Neuropsychology Handbook, Vol. 1, Foundations and Assessment*, 2nd ed., New York:Springer Publishing Company (1997), which is hereby incorporated by reference.

Clinical guidelines for patient selection are based on the patient's functional disturbance. For example, the patient's cognitive impairment may be slowing (or, in a severe case, dementia), as manifested in the patient's decreased attention, impaired intention, and decreased working memory. Alternatively, the patient may exhibit primary failure to initiate action despite interaction when stimulated. Patient selection in the clinical setting would also depend, in part, on prognostic signs, such as the presence of spontaneous fluctuations in functional level, modulation of functional level by external stimulation, or reliably produced modulation by internally generated stimulation.

As indicated above, the present invention relates to a method of treating a conscious patient having impaired cognitive function. Conscious, as used herein, has the conventional meaning, as set forth in Plum, et al., *The Diagnosis of Stupor and Coma*, CNS Series, Philadelphia:Davis (1982), which is hereby incorporated by reference. Conscious patients include those who have a capacity for reliable, reproducible, interactive behavior evidencing awareness of self or the environment. Conscious patients include patients who recover consciousness with less severe brain injury but who, because of their impaired cognitive function, do not reach independent living and remain in nursing facilities. Conscious patients do not include those who exhibit wakefulness but lack interaction (e.g., those deemed to be in a persistent vegetative state). A significant percentage, roughly 20% of patients who suffer severe brain damage remain conscious with preserved capacity for memory, attention, intention, and awareness. This is in contrast to patients who suffer from states of global unconsciousness, as indicated by conditions such as coma, persistent vegetative states, apallic state, coma vigil, and severe dementia.

Since adult patients in their twenties to forties have the most to gain from treatment and represent the greatest cost to society if left untreated, they would be preferred candidates for the intervention of the present invention. However, patients younger or older than those in the above age range would also benefit from the practice of the present invention. Although, in the early stages of clinical application, the method of the present invention will likely target more seriously compromised patients, it is believed that, ultimately, the method will have wider application to patients with mild to moderate cognitive impairment following brain injury as well. Patients suffering from post encephalitic parkinsonism or other disease processes which include oculogyric crises as a symptom are envisioned as being one class of patients who can be treated using the method of the present invention.

Once the conscious patient having impaired cognitive function is selected, electrical stimulation is applied to at least a portion of the patient's intralaminar nuclei under conditions effective to relieve the patient's impaired cognitive function.

Figure 8:
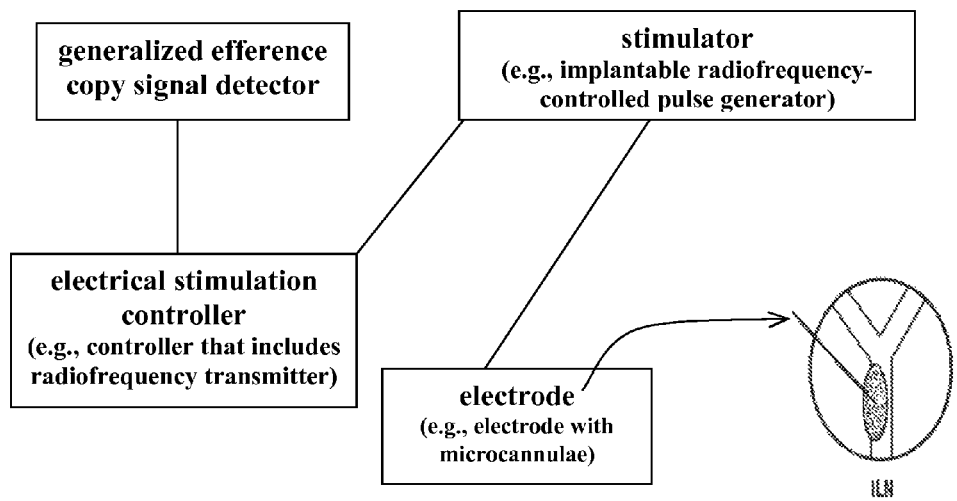
FIG. 8 is a schematic diagram illustrating an apparatus according to the present invention.

Generally, stimulation of the patient's intralaminar nuclei involves contacting the intralaminar nuclei with an electrode capable of delivering an electrical signal to the patient's intralaminar nuclei. See FIG. 8. A variety of electrodes can be employed for delivering the stimulation. For example, suitable electrodes include the deep brain stimulation electrodes used in Katayama, "Characterization and Modification of Brain Activity with Deep Brain Stimulation in Patients in a Persistent Vegetative State: Pain-Related Late Positive Component of Cerebral Evoked Potential," *Pace*, 14:116-121 (1991), which is hereby incorporated by reference, and the Medtronic DBS 3280 (available from Medtronic, Minneapolis, Minn.), which has a flexible TEFLON-SILASTIC™ coated, platinum iridium electrodes with 4 contacts, 4 mm tips, 2 mm, mean tip separation, and an impedance of 5-7 kΩ within the brain, described in Velasco et al., "Electrocortical and Behavioral Responses Produced By Acute Electrical Stimulation of the Human Centromedian Thalamic Nucleus," *Electroencephalography and Clinical Neurophysiology*, 102: 461-471 (1997) ("Velasco"), which is hereby incorporated by reference. Preferably the electrode is an implantable multipolar electrode with either an implantable pulse generator that can be a radiofrequency controlled device operated by an external transmitter. Preferably, the multipolar electrode contacts should allow for adjustment of frequency (or "rate"), amplitude, and pulse width within at least the following respective ranges: about 2-200 Hz, about 0.1-10 Volts, and about 50-500 microseconds. More preferably, the multipolar electrode contacts allow for adjustment in a broader range than those recited above, particularly toward higher intensities. Such preferred electrodes include a Medtronic 3387 electrode (available from Medtronic, Minneapolis, Minn.) and are described, for example, in Benabid et al., "Chronic Electrical Stimulation of the Ventralis Intermedius Nucleus of the Thalamus As a Treatment of Movement Disorders," *J. Neurosurgery*, 84:203-214 (1996), which is hereby incorporated by reference. In some situations, it may be desirable to use an electrode capable of delivering pharmacological agents to the patient's subcortical structures. Such electrodes include electrodes with microcannulae and are described in, for example, Hikosaka et al., "Modification of Saccadic Eye Movements by GABA-related Substances. I. Effect of Muscimol and Bicuculline in Monkey Superior Colliculus." *J. Neurophysiology*, 53:266-291 (1985), which is hereby incorporated by reference. Examples of suitable pharmaceutical agents which can be used in conjunction with the electrical stimulation methods of the present invention include known excitatory and inhibitory transmitters that influence intralaminar nuclei function. Excitatory transmitters would preferably include acetylcholine ("Ach"), noradrenaline ("NE"), and/or serotonin ("5-HT") or analogues thereof. Inhibitory transmitters would include primary gamma-aminobutyric acid ("GABA") or analogs thereof. Other amino acid transmitters known to affect the intralaminar nuclei, such as adenosine or glutamate, can also be used.

The electrode can be contacted with the patient's intralaminar nuclei by the methods conventionally employed for embedding or emplacing electrodes for deep brain electrical stimulation in other thalamic nuclei. Such methods are described in Tasker et al., "The Role of the Thalamus in Functional Neurosurgery," *Neurosurgery Clinics of North America*, 6(1):73-104 (1995) ("Tasker"), which is hereby incorporated by reference. Briefly, the multi-polar electrode or electrodes are introduced via burr holes in the skull. The burr holes are placed based on the particular region of the intralaminar nuclei to be contacted. Preferably, prior to the introduction of the implantable multi-polar electrode(s), a detailed mapping with microelectrode and microstimulation following standard methods is carried out as described in Tasker, which is hereby incorporated by reference. Briefly, for each subdivision of the intralaminar nuclei, a preferred trajectory of approach optimizing the safety of entry point and maximal number of identifiable physiological landmarks in the responses of cell groups encountered along the trajectory into the desired region or regions of the intralaminar nuclei can be identified by one skilled in the art. This can be done, for example, by following the methods and catalogued physiological responses of different human thalamic cell groups described in Tasker, which is hereby incorporated by reference. Initial mapping of the path for the stimulating electrode(s) can, therefore, be carried out via a combination of detailed single-unit recording of receptive field ("RF") properties of the cells encountered along the trajectory, projective fields ("PF") mapped by microstimulation of the same cell groups, and comparison with known RF and PF responses in the human thalamus. Similarly, evoked potentials can be recorded and, for the intralaminar nuclei, have several characteristic signatures identifiable from scalp surface recording as discussed in Velasco and Tasker, which are hereby incorporated by reference. For this mapping, microstimulation, using tungsten microelectrodes with impedances of roughly 1.5 megaohms, every 1 mm at threshold of up to 100 microamperes with short trains of 300 Hz pulses of 0.2 millisecond pulse width are employed as described in Tasker, which is hereby incorporated by reference. Typically, an on-line data base of RF and PF information along the trajectory and stereotactic coordinates derived, for example, from Schaltenbrand et al., *Introduction to Stereotaxis with an Atlas of the Human Brain*, Stuttgart:Thieme (1977), which is hereby incorporated by reference, or by computed mapping techniques, such as those described in Tasker et al., "Computer Mapping of Brainstem Sensory Centres in Man," *J. Neurosurg.* 44:458-464 (1976), which is hereby incorporated by reference, can be used, either with or without a magnetic resonance imaging ("MRI")-based stereotactic apparatus. To carry out the above methods, a patient would typically remain conscious with application of local anesthesia or mild sedation. However, in cases where a patient is not sufficiently cooperative to remain conscious during the procedure, the above-described approach can be modified to allow the operation to be completed under general anesthesia.

The electrical stimulation can be continuous, intermittent, or periodic. The range of stimulation frequencies and intensity of stimulation will depend on several factors: impedance of the electrode once in the brain, excitation properties of cells which may differ within subdivisions of the intralaminar nuclei, the type of induced physiologic responses sought for a particular patient, and interindividual variation. While higher frequency ranges are thought to be preferred, lower frequencies will also be employed. Suitable stimulation frequencies range from about 1 Hz to 1 kHz; preferably, from about 10 Hz to about 500 Hz; and, more preferably, from about 50 Hz to about 250 Hz. However, higher frequencies can be utilized where amplitude or frequency modulated signals are used.

Typically, the electrode is connected to an insulated conductor which leads to an external connector plug which is removably connected to a mating plug which is, in turn, connected to a voltage control and pulse generator. The pulse generator produces a selected pulse train, and the voltage control provides a selected current amplitude or voltage to the waves of the pulse train. The signal pulse generator should preferably be capable of generating voltage wave trains of any desired form (sine, square wave, spike, rectangular, triangular, ramp, etc.) in a selectable voltage amplitude in the range from about 0.1 volts to about 10 volts and at selectable frequencies as set forth above. In practice, the pulse train and voltage amplitudes employed will be selected on a trial and error basis by evaluating a patient's response to various types and amplitudes of electrical stimulation over a time course of from about 1 to about 12 months. For example, after implanting the electrode in the patient's intralaminar nuclei, stimulation with a voltage within the range of from about 0.1 to about 10 volts or higher, a rate within the range of from about 50 to about 250 Hz, and a pulse width within the range of from about 50 to about 500 microseconds is applied for from about 8 to about 12 hours a day. During and after the implantation of the electrode, the parameters of the stimulation (voltage, pulse width, and frequency) are adjusted to optimize the patient's interactive behavior.

Intralaminar nuclei are a small set of nuclei located in the paramedian thalamus. The intralaminar nuclei can be divided into an anterior group and a posterior group. FIG. 1 illustrates the anatomical connections of the intralaminar nuclei with distributed circuits underlying arousal, attention, intention, working memory, and gaze and motor control. The anterior group projects widely throughout the neocortex to primary sensory and motor areas and association cortices, while the posterior group projects mainly to sensory-motor and premotor areas and striatal targets. The anterior IL group includes the central lateral nucleus ("CL"), which projects to the frontal eye field ("FEF"), motor cortex, and, more heavily, to the posterior parietal cortex ("PPC"). The paracentralis ("Pc") nucleus projects to the prefrontal cortex (with heavier projection than CL) and very strongly to the inferior parietal lobe and visual association cortices. The central medial ("CeM") nucleus, which also projects to the prefrontal and visual association cortices, also projects to the cingulate cortex and pregenual areas and to the medial cortical surface and orbitofrontal cortex. Included within the meaning of intralaminar nuclei, as used herein, is the Paraventricular nucleus ("Pv"), which is strongly associated with the limbic system, and midline thalamic nuclei. Projections to prefrontal cortex ("PFC") and anterior cingulate cortex arise, as well, from the anterior intralaminar group. The CL is also known to project to the primary visual cortex in the cat and monkey. The posterior group is dominated by the centromedian-parafascicularis complex ("Cm-Pf"), which strongly projects to areas 6 and 4. In primates, the Cm-Pf undergoes a notable expansion, and the CL also expands and develops further subdivisions. This system projects strongly to the caudate (from Pf), putamen (from Cm nuclei of the basal ganglia), and prefrontal and parietal association cortices. A small projection (Pf) also goes to the FEF. The intralaminar nuclei projections to the striatum per se are considered the principle efferent connections of the intralaminar nuclei and include anterior group projections to the caudate, as well. Thus, the intralaminar nuclei (including the midline nuclei) are believed to be in a preferred position to modulate the large thalamo-cortical-basal ganglia loops, especially to synchronize their function (Groenewegen et al., "The Specificity of the "Nonspecific" Midline and Intralaminar Thalamic Nuclei," *Trends in Neuroscience* 17:52-66 (1994) ("Groenewegen"), which is hereby incorporated by reference.

The intralaminar nuclei receive ascending inputs from several components of the ascending reticular arousal system, including the pedunculopontine cholinergic group (lateral dorsal tegmentum), mesencephalic reticular formation, locus ceruleus, and dorsal raphe. Thus, the intralaminar nuclei are targets of modulation by a wide variety of neurotransmitter agents, including acetylcholine (pendunculopontine, lateral dorsal tegmentum, and mesencephalic reticular formation neurons), noradrenaline (locus ceruleus) serotonin (raphe nuclei), and histamine (hypothalamus). Also received by the intralaminar nuclei are nociceptive, cerebellar, tectal, pretectal, and rhinencephalic inputs. Descending inputs reciprocally relate components of the intralaminar nuclei with their cortical projections.

Although each cell group within the intralaminar nuclei projects to many separate cortical targets, each neuron of the intralaminar nuclei has a narrowly elaborated projection and receives its cortical feedback from the same restricted area. The reciprocal projections between the intralaminar nuclei and cortex have a distinctive laminar pattern that differs from the more well-known pattern of the reciprocal projections of the relay nuclei. The intralaminar nuclei neurons synapse in Layer I on the terminal dendritic tufts of layers III and V pyramidal cells and in layers V and VI, whereas neurons of the relay nuclei terminate primarily in cortical layers III and IV. Feedback to intralaminar nuclei neurons originates in Layer V, but feedback to the relay nuclei originates in Layer VI. In the cat, the dominant corticothalamic input to the CL originates in the PFC, whereas the visual areas, including area 17, also project directly to the CL.

As used herein, intralaminar nuclei also include paralamellar regions, such as parts of the medial dorsal ("MD") nucleus and the midline nuclei (which are sometimes distinguished from the intralaminar nuclei but, for purposes of the present application, are not).

FIGS. 2A-2E illustrate intralaminar nuclei subdivisions suitable for stimulation in accordance with the practice of the present invention. Table 1 sets forth the meanings of the abbreviations used in FIGS. 2A-2E (See Buren et al., *Variations and Connections of the Human Thalamus*, New York: Springer-Verlag (1972), which is hereby incorporated by reference).

TABLE 1

| Term | Sagittal | Horizontal | Transverse |
|---|---|---|---|
| A - N. amygdalae | S - L 12.0-22.0 | | T - A 20.3 (PC)-10.9 (PC) |
| Ad - N. anterodorsalis | S - L 3.0 | H - S 13.2 | T - A 20.3 (PC)-14.1 (PC) |
| Apr - N. anteroprincipalis | S - L 3.0-9.0 | H - S 13.2-6.3 | T - A 23.4 (PC)-10.9 (PC), 4.7 (PC) |
| B - N. basalis | S - L 6.0-22.0 | H - I 4.5-8.1 | T - A 23.4 (PC)-10.9 (PC) |
| Bcj - Brachium conjunctivum | | H - I 8.1 | |
| Bcoi - Brachium colliculi inferioris | S - L 9.0 | H - I 4.5 | T - P 1.6 (PC), 4.7 (PC) |
| Bcos - Brachium colliculi superioris | S - L 9.0 | H - I 4.5 | |
| Ccls - Corporis callosi splenium | S - L 2.0-3.0 | | |
| Cd - N. caudatus | S - L 6.0, 12.0-25.0 | H - S 17.0-13.2 | T - A 23.4 (PC)-P 4.7 (PC) |
| Cemc - N. centralis magnocellularis | S - L 9.0 | H - S 2.7 | T - A 7.8 (PC)-1.0 (PC) |
| Cepc - N. centralis parvocellularis | S - L 9.0-12.0 | H - S 6.3-I 0.9 | T - A 7.8 (PC)-1.0 (PC) |
| Cl - Claustrum | | H - S 17.0, 9.7 | T - A 23.4 (PC) |
| Cm - Corpus mammillare | S - L 2.0, 2.5 | | T - H 1 (PC) |
| Cma - Commissura anterior | S - L 2.0, 6.0, 12.0-25.0 | H - S 2.7-I 8.1 | T - A 23.4 (PC) 17.2 (PC) |
| Cmp - Commissura posterior | S - L 2.0, 3.0 | H - S 2.7, I 0.9 | T - P 1.6 (PC) |
| CnA - Cornu Ammonis | S - L 19.0-25.0 | H - I 0.9, I 8.1 | T - A 7.8 (PC)-1.0 (PC) |
| Co - N. commissuralis | S - L 2.0-2.5 | H - S 2.7 | T - A 20.3 (PC)-10.9 (PC) |
| Cos - Colliculus superior | S - L 2.0-6.0 | H - I 0.9, 4.5 | T - P 4.7 (PC) |
| Dc - N. dorsocaudalis | S - L 12.0-19.0 | H - S 13.2, 9.7 | T - A 7.8 (PC)-1.6 (PC) |
| Do - N. dorsoralis | S - L 9.0-19.0 | H - S 17.0-9.7 | T - A 17.2 (PC)-7.8 (PC) |
| Dsf - N. dorsalis superficialis | S - L 6.0-12.0 | H - S 17.0, 13.2 | T - A 10.9 (PC)-4.7 (PC) |
| Edy - N. endymalis | S - L 2.0, 2.5 | H - I 0.9 | T - A 17.2 (PC)-10.9 (PC), 4.7 (PC) |
| F - Fornix | S - L 2.0-3.0 | H - S 17.0-I 8.1 | T - A 23.4 (PC)-14.1 (PC), P 1.6 (PC), 4.7 (PC) |
| Fa - N. fasciulosus | S - L 3.0, 6.0 | H - S 2.7-I 0.9 | T - A 23.4 (PC)-17.2 (PC) |
| Glmc - Corpus geniculatum laterale, magnocellularis | S - L 19.0-25.0 | H - I 4.5, 8.1 | T - A 1.6 (PC), P 1.6 (PC) |
| Glpc - Corpus geniculatum laterale, parvocellularis | S - L 19.0-25.0 | H - I 4.5, 8.1 | T - A 1.6 (PC), P 1.6 (PC) |
| Gmmc - Corpus geniculatum mediale, magnocellularis | S - L 12.0 | H - I 4.5 | T - P 1.6 (PC) |
| Gmpc - Corpus geniculatum mediale, parvocellularis | S - L 12.0, 16.0 | H - I 0.9, 4.5 | T - A 1.6 (PC), P 1.6 (PC) |
| Grceme - Grisca centralis mesencephali | S - L 2.0-3.0 | H - I 4.5, 8.1 | T - P 1.6 (PC), 4.7 (PC) |
| cf $H_1$ - Campus Forelii $H_1$ | S - L 6.0, 9.0 | H - I 4.5 | T - A 10.9 (PC) |
| cf $H_2$ - Campus Forelii $H_2$ | S - L 6.0, 9.0 | H - I 4.5 | T - A 10.9 (PC) |
| H1 - N. habenularis lateralis | S - L 3.0 | H - S 6.3, 2.7 | T - A 1.6 (PC) |
| Hm - N. habenularis medialis | S - L 2.0-3.0 | H - S 6.3, 2.7 | T - A 1.6 (PC) |
| Hpth - Hypothalamus | S - L 2.0-6.0 | H - I 0.9-8.1 | T - A 23.4 (PC)-10.9 (PC) |
| iLa - N. intralameliaris | S - L 2.0-12.0 | H - S 13.2-2.7 | T - A 17.2 (PC)-1.6 (PC) |
| Is - N. interstitialis (Cajal) | | | T - A 1.6 (PC), P 4.7 (PC) |
| Li - N. limitans | S - L 6.0-12.0 | H - I 0.9 | T - P 1.6 (PC) |
| Ll - Lemniscus lateralis | | | T - P 1.6 (PC), 4.7 (PC) |
| Lm - Lemniscus medialis | | H - I 4.5, 8.1 | |
| Lpo - N. lateropolaris | S - L 6.0-16.0 | H - S 13.2-I 0.9 | T - A 23.4 (PC)-14.1 (PC) |
| M - N. medialis | S - L 2.0-9.0 | H - S 13.2-2.7 | T - A 17.2 (PC)-1.6 (PC) |
| NIII - N. oculomotorius | S - L 2.0 | | T - A 1.6 (PC)-P 4.7 (PC) |
| NVme - N. nervi trigemini mesencephalicus | | | T - P 4.7 (PC) |
| NEW - N. Edinger Westphal | S - L 2.0 | | T - A 4.7 (PC)-P 4.7 (PC) |
| Pf - N. parafascicularis | S - L 6.0 | H - I 0.9 | T - A 7.8 (PC)-1.6 (PC) |
| Pi - Pincal | S - L 2.0-3.0 | | T - P 4.7 (PC) |
| Pl - Pallidum laterale | S - L 9.0-22.0 | H - S 6.3-I 4.5 | T - A 23.4 (PC)-7.8 (PC) |
| Pm - Pallidum mediale | S - L 9.0-19.0 | H - S 2.7-I 4.5 | T - A 23.4 (PC)-10.9 (PC) |
| Pma - N. paramedianus anterior | S - L 2.0-2.5 | H - S 2.7 | T - A 20.3 (PC)-10.9 (PC) |
| Pmp - N. paramedianus posterior | S - L 2.0-2.5 | H - S 2.7 | T - A 7.8 (PC)-1.6(PC) |
| Ppd - N. peripeduncularis | S - L 12.0 | H - I 4.5, 8.1 | T - A 1.6 (PC) |
| Pret - Area pretectalis | S - L 6.0 | H - I 0.9, 4.5 | T - P 1.6 (PC) |
| PrG - N. paraegeniculatus | S - L 19.0-22.0 | H - I 4.5, 8.1 | T - A 1.6 (PC) |
| Pt - N. parataenialis | S - L 2.0-3.0 | H - S 9.7-2.7 | T - A 20.3 (PC)-7.8 (PC) |
| Pui - N. pulvinaris intergeniculatus | S - L 12.0 | H - I 4.5 | T - P 1.6 (PC) |

TABLE 1-continued

| Term | Sagittal | Horizontal | Transverse |
|---|---|---|---|
| Pul - N. pulvinaris lateralis | S - L 16.0-22.0 | H - S 13.2-I 0.9 | T - A 1.6 (PC)-P 4.7 (PC) |
| Pum - N. pulvinaris medialis | S - L 6.0-16.0 | H - S 13.2-I 0.9 | T - A 1.6 (PC)-P 4.7 (PC) |
| Puo - N. pulvinaris oralis | S - L 12.0 | H - S 6.3, 2.7 | T - A 1.6 (PC) |
| Put - Putamen | S - L 19.0-25.0 | H - S 13.2-I 8.1 | T - A 23.4 (PC)-7.8 (PC) |
| Pv - N. paraventricularis hypothalami | S - L 2.5, 3.0 | H - I 0.9-8.1 | T - A 23.4 (PC), 20.3 (PC) |
| R - N. reticularis | S - L 6.0-25.0 | H - S 17.0-I 0.9 | T - A 23.4 (PC)-4.7 (PC), P 1.6 (PC), 4.7 (PC) |
| Ru - N. ruber | S - L 2.0-6.0 | H - I 4.5-8.1 | T - A 7.8 (PC)-1.6 (PC) |
| Smth - Stria medullaris thalami | S - L 2.0-3.0 | H - S 9.7, 6.3 | T - A 23.4 (PC)-1.6 (PC) |
| Sn - Substantia nigra | S - L 6.0-12.0 | H - I 8.1 | T - A 14.1 (PC)-1.6 (PC) |
| So - N. supraopticus hypothalami | S - L 3.0-6.0, 12.0 | | T - A 23.4 (PC), 20.3 (PC) |
| Sth - N. subthalamicus | S - L 6.0-12.0 | H - I 4.5, 8.1 | T - A 14.1 (PC)-7.8 (PC) |
| Tl - Nucleus tuberis lateralis | S - L 6.0 | | |
| TM - Tractus Menerti | S - L 2.0-6.0 | H - S 2.7-I 8.1 | T - A 7.8 (PC)-1.6 (PC) |
| Tmth - Tractus mammillothalamicus | S - L 2.5-6.0 | H - S 6.3-I 8.1 | T - A 17.2 (PC), 14.1 (PC) |
| TO - Tractus opticus | S - L 2.5-22.0 | | T - A 20.3 (PC)-4.7 (PC) |
| Vce - N. ventrocaudalis externus | S - L 16.0-19.0 | H - S 9.7-I 0.9 | T - A 7.8 (PC)-1.6 (PC) |
| Vci - N. ventrocaudalis internus | S - L 12.0-16.0 | H - S 6.3-I 0.9 | T - A 7.8 (PC)-1.6 (PC) |
| Vcpc - N. ventrocaudalis parvocellularis | S - L 9.0-12.0 | H - I 0.9 | T - A 7.8 (PC), 4.7 (PC) |
| Vcv - N. ventrocaudalis ventralis | S - L 16.0 | H - I 4.5 | T - A 7.8 (PC)-1.6 (PC)) |
| Vim - N. ventrointermedius | S - L 9.0-19.0 | H - S 6.3-I 0.9 | T - A 10.9 (PC)-4.7 (PC) |
| Voe - N. ventrooralis externus | S - L 9.0-16.0 | H - S 13.2-I 0.9 | T - A 17.2 (PC)-7.8 (PC) |
| Voi - N. ventrooralis internus | S - L 6.0 | H - S 9.7-I 0.9 | T - A 14.1 (PC), 10.9 (PC |
| Zi - Zona incerta | S - L 6.0-16.0 | H - I 4.5 | T - A 17.2 (PC)-4.7 (PC) |

For example, the stimulated intralaminar nuclei subdivisions can include the centromedian-parafasicularis or the central lateral or both. Alternatively, the stimulated portion of the patient's intralaminar nuclei can be selected so that it does not include the centromedian-parafasicularis, the central lateral, or either the centromedian-parafasicularis or the central lateral nuclei.

The electrical stimulation can be applied to the patient's entire intralaminar nuclei or to one or more portions of the patient's intralaminar nuclei. In addition to being applied to the patient's intralaminar nuclei or portion thereof, the electrical stimulation can also extend to other regions of the brain. Preferably, the electrical stimulation is applied only to the patient's intralaminar nuclei or portion thereof without stimulating other regions of the patient's brain. For example, the electrical stimulation can be applied to all portions of the patient's intralaminar nuclei except the centromedian-parafasicularis, except the central lateral, or except both the central lateral and centromedian-parafasicularis.

The method of the present invention can further comprise selecting one or more subdivisions of the patient's subcortical structures integrated in the generation and control of generalized efference copy signals for stimulation. Electrical stimulation is again followed by detection of internally generated movement of the patient and, in response, control of the electric stimulation. In particular, the subdivision to be stimulated can be one which modulates the specific cognitive function which is impaired in the patient. For example, Table 2 sets forth various subdivisions of the intralaminar nuclei and the specific cognitive function with which each is associated.

TABLE 2

| Specific ILN Subdivision | Cognitive Function Impairment |
|---|---|
| centromedian-parafasicularis | attention deficits, anosognosia, working memory deficits, intentional deficits, nonsensory neglect, akinesia, frontal lobe damage |
| central lateral | perceptual impairment, sensory neglect, visuomotor impairment, working memory deficits, attentional deficits, anosognosia |
| paracentralis | working memory deficits, apathy, emotional dyscontrol |
| paraventricularis | loss of awareness of emotional/limbic signals |
| central medial | apathy, emotional dyscontrol, intentional deficits |

Further details regarding the identification of intralaminar nuclei subdivisions which modulate specific cognitive function can be found in, for example, Macchi et al., "The Thalamic Intralaminar Nuclei and the Cerebral Cortex," pp. 355-389, in Jones et al., eds., *Cerebral Cortex, Vol. 5*, New York: Plenum Press (1986), Castaigne et al., "Paramedian Thalamic and Midbrain Infarcts: Clinical and Neuropathological Study," *Ann. Neurol.*, 10:127-148 (1980), and Purpura et al., "The Thalamic Intralaminar Nuclei: A Role in Visual Awareness," *The Neuroscientist,* 3:8-15 (1997) ("Purpura"), which are hereby incorporated by reference. Thus, by knowing the specific cognitive function or functions impaired in a particular patient, the preferred subdivision of the particular patient's intralaminar nuclei to receive electrical stimulation can be determined.

In cases where the patient suffers from post-encephalitic parkinsonism or other disease processes which include oculogyric crises as a symptom, it is believed that the preferred intralaminar nuclei subdivision is the central medial.

Once the particular subdivision to be stimulated is selected, that subdivision and, optionally, others are stimulated as described above. That is, electrical stimulation can be applied to the selected subdivision only, or, alternatively, electrical stimulation can be applied to the selected subdivision as well as other subdivisions of the patient's intralaminar nuclei. Stimulation can be applied to the selected subdivision and optional other subdivisions of the intralaminar nuclei in either or both brain hemispheres.

Preferably, the intralaminar nuclei subdivision which is to receive electrical stimulation is one which projects to an area of the brain which has reduced baseline function but which also exhibits increased function during periods of external stimulation or internally generated stimulation, such as patient's self-generated activity (e.g., head turning).

In many cases, patients with cognitive impairments following brain injury can have their cognitive function modulated by various forms of external stimulation. For example, in some patients, stimulation of the brainstem vestibular system with cold water caloric stimulation of the external ear canal, such as described in Gainotti, "The Role of Spontaneous Eye Movements in Orienting Attention and in Unilateral Neglect," pp. 107-113, in Robertson et al., eds., *Unilateral Neglect: Clinical and Experimental Studies*, Hove, United Kingdom:Lawrence Erlbaum Associates, Publishers (1993) and Vallar et al., "Modulation of the Neglect Syndrome by Sensory Stimulation," pp. 555-578, in Thier et al., eds., *Parietal Lobe Contributions to Orientation in 3D Space*, Heidelberg, Germany:Springer-Verlag (1997) ("Vallar"), which are hereby incorporated by reference, generates transient but profound recovery of multiple cognitive functions including self-awareness, intention, and perceptual awareness. Other external stimulation that may modulate cognitive function, would include alteration of trunk, head, or limb position signals, such as a vibrational stimulation of the sternocleidomastoid muscle.

Similarly, some patients with less severe global impairments of consciousness discover strategies to self-generate behaviors that assist in supporting their cognitive or perceptual function. For example, some patients with visual agnosias who have visual perceptual problems discover that self-generated rhythmic head movements or hand tracing movements improve their visual awareness and cognitive skills in identifying figures. These self-generated rhythmic head and hand movements are described in Farah, *Visual Agnosia*, Cambridge, Mass.:MIT Press (1990), which is hereby incorporated by reference.

It is believed that the capacity to modulate cognitive function by external or internal stimulation in these patients demonstrates that certain brain activations can optimize their function. In the case of vestibular stimulation, it is believed that the intralaminar nuclei are directly implicated by their strong inputs from the vestibular nuclei. Although the present invention is not intended to be limited by the mechanism by which it operates, it is believed that the intralaminar nuclei's role in supporting these function relates to the generation of event-holding functions that may promote interaction across the cortex, possibly by enhancing synchronization, as described in Purpura. One theory of the present invention is that similar event-holding functions tied to head, hand, trunk, or other bodily coordinates are generated by intralaminar nuclei stimulation and account for the improved cognitive function seen in patients who are externally or internally stimulated. Whether or not such other modulations are directly tied to intralaminar nuclei stimulation, functional studies in an individual patient, such as those carried out in Bottini et al, "Modulation of Conscious Experience by Peripheral Sensory Stimuli," *Nature*, 376:778-781 (1995), which is hereby incorporated by reference, can be used to identify specific cortical regions that are modulated as an initial step in applying the method of the present invention.

Although the above described method for selecting a subdivision of the patient's intralaminar nuclei to which to apply electrical stimulation in accordance with the present invention is acceptable, in many cases, it is preferred to determine, on a individual basis, which areas of the brain have reduced baseline function, and then to correlate the area of the brain having reduced baseline function with an intralaminar nuclei subdivision which projects thereto. As one skilled in the art would recognize, determining areas of the brain which have reduced baseline function can be carried out advantageously using quantitative metabolic information obtained from a FDG-PET study of resting brain metabolism; using electromagnetic indicators of regional functional activity; anatomically, physiologically, or metabolically; or using combinations of these methods. As used herein, baseline brain function is defined within the patient and across a database of normal values for resting cerebral metabolism and is typically measured in terms of glucose uptake and utilization. One particularly useful gauge of baseline brain function is the regional cerebral metabolic rate as measured using fluorodeoxyglucose ("rCMRgluc"). This is quantitated by fluorodeoxyglucose-PET measurements and compared across brain structures within the patient's brain and against normative values for particular brain regions. Further details regarding assessing baseline brain function are described in, for example, Mazziota, ed., *Clinical Brain Imaging*, CNS Series, Philadelphia:Davis (1992), which is hereby incorporated by reference. Once the portion of the brain having reduced baseline function is identified, the portion can be correlated with the intralaminar nuclei ("ILN") subdivision which projects to this region, for example, by using Table 3.

TABLE 3

| Specific ILN Subdivision | Primary Cortical Targets |
| --- | --- |
| centromedian-parafasicularis | prefrontal cortex, premotor cortex, parietal cortex |
| central lateral | prefrontal cortex, parietal cortex, visual association cortex, motor cortex |
| paracentralis | prefrontal cortex, orbitofrontal cortex |
| paraventricularis | amydala, limbic system |
| central medial | orbitofrontal cortex |
| paralam MD | prefrontal cortex |
| midline nuclei | hippocampus, limbic system |

Further details regarding the correlation of areas of the brain to the intralaminar nuclei subdivisions which project thereto can be found in, for example, Jones et al., eds., *The Thalamus*, Amsterdam:Elsevier (1995), which is hereby incorporated by reference. When a subdivision is selected in this manner, electrical stimulation can be applied to the selected subdivision only, or, alternatively, it can be applied to the selected subdivision and, in addition, to other subdivisions of the patient's intralaminar nuclei.

As indicated above, electrical stimulation can be applied to the entire group of intralaminar nuclei or to one, two, or more specific subdivisions thereof. Stimulation can be applied to the one, two, or more specific subdivisions in either or both brain hemispheres. In some cases, it can be advantageous to apply electrical stimulation to two or more subdivisions of the intralaminar nuclei which modulate separate cortical regions. As used herein, cortical regions are considered to be separate when they are not contiguous on the cortical mantle or they are considered separate in function based on known anatomical or physiological characteristics of cells within their borders. For example, the patient's central medial and centromedian-parafasicularis intralaminar nuclei subdivisions, which respectively project strongly to the orbitofrontal and premotor regions of the cortex, can be stimulated. Where two or more subdivisions of the intralaminar nuclei are stimulated, both can lie in the same thalamus. Alternatively, at least one of the two or more subdivisions of the intralaminar nuclei can lie in the left thalamus while at least one of the two or more subdivisions of the intralaminar nuclei lies in the right thalamus. Preferably, at least one of the two or more subdivisions and, more preferably, at least two of the two or more subdivisions of the intralaminar nuclei to which electrical stimulation is applied modulates the specific cognitive function which is impaired in the patient.

Where two or more subdivisions of the patient's intralaminar nuclei are electrically stimulated periodically and at the same frequency, such stimulation can be completely in phase, partially in phase and partially out of phase, or completely out of phase. When such stimulation is substantially entirely in phase, it is said to be synchronized. In a preferred embodiment of the present invention, the electrical stimulation applied to two or more subdivisions of the patient's intralaminar nuclei is synchronized. It is believed that activation of separate cortical regions by common intralaminar nuclei inputs promotes coordinated processing in these separated cortical regions because of the strong capacity of these intralaminar inputs to generate depolarization of neurons in the supragranular layers (upper) of the cerebral cortex. It is believed that such strong depolarization generates improved synchronization of neuronal activity across cortical regions. This improved synchronization may result from high frequency oscillations excited by these inputs or sustained enhancement of neural activity seen in the form of broadband activity or increased average power across a cortical region. More particularly, the method of the present invention can be optimized by monitoring regional and intrahemispheric changes in brain waves (e.g., changes in absolute power, relative power, and/or intra- and/or inter-regional coherence) as measured by using conventional techniques (e.g., electroencephalogram (EEG) or magnetoencephalogram (MEG) techniques)) or by monitoring regional and intrahemispheric changes in metabolic activity. As indicated above, metabolic activity can be assessed using conventional methods (e.g., positron emission tomography ("PET") or FDG-PET).

The result of intralaminar nuclei stimulation under one aspect of the present invention is that correction of functional disconnections of brain regions by release of inhibition of remaining cortical or subcortical regions may be achieved by stimulation of the appropriately connected intralaminar nuclei; such release of inhibition may increase metabolic activity in suppressed areas. Alternatively, such stimulation may result in an alteration of population activity of many neurons in a local cortical area that improves information transfer or processing capacities of the neurons in that region (for example, by sharpening their receptive fields). Under another aspect of the present invention, synchronization of stimulated areas may facilitate a broader integration of cortical processing via synchronization of activity within the intralaminar nuclei of each thalamus and promote a global integrative process at the level of the cortex. Similarly, intralaminar nuclei connected to cortical areas known to be important for specific cognitive functions independent of a patient's particular injury, but selected by the patient's behaviorally evidenced impairment, may be selected for stimulation.

Selection of a particular strategy of intralaminar nuclei stimulation for a given patient will depend on several features including the specific cortical regions a given subdivision of the intralaminar nuclei projects to, particular stimulation parameters, evidence of modulation of cognitive function by external stimulation, internally generated stimulation (e.g., head turning), or spontaneously, and the patient's underlying brain damage and/or behavioral dysfunction Optimization of the preferred method of the present invention involves promoting coordinated information processing or enhanced participation in integrated brain function of cortical regions innervated by intralaminar nuclei. If possible, this optimization can be based on evidence of improved function with reliable external (or internal) stimulation procedures or indexed by strong clinical inferences and functional anatomic information based on areas of identified hypometabolism or anatomical disconnection.

As one skilled in the art will recognize, optimization of the method of the present invention can be achieved by varying specific stimulation parameters (such as intensity, frequency, pulse width, on time and off time, and duty cycle) while monitoring cognitive function as assessed by standard neuropsychologic instruments of working memory, attention, and/or intention. Optimization can also be effected by monitoring specific regional and intrahemispheric changes in distribution of signal power and coherence within the frequency spectrum.

It is believed that the mechanism which permits treatment of patients having impaired cognitive function with electrical stimulation of his or her intralaminar nuclei is based, in part, on applicants' newly theorized role for the intralaminar nuclei in cognitive operations, which is set forth in Purpura, which is hereby incorporated by reference. Although the present invention is not meant in any way to be limited by the mechanism in which it operates, for example, as set forth in Purpura, it is believed that the proposed mechanism may assist in optimizing the method of the present invention.

In another aspect of the present invention, coordination of function across cortical regions in a patient is improved by applying electrical stimulation to two or more subdivisions of the patient's intralaminar nuclei. Improved coordination of function across cortical regions, as used herein, is meant to include improved functional interactions of specific cortical regions within and across left and right hemispheres, such as those discussed above in regard to the effects of vestibular stimulation. In this method, the two or more subdivisions of the patient's intralaminar nuclei modulate separate cortical regions. Preferably, the electrical stimulation applied to the two or more subdivisions of the intralaminar nuclei is synchronized or periodic, more preferably, synchronized and periodic. Suitable frequencies for use in the method of this aspect of the present invention range from about 1 Hz to 1 kHz; preferably, from about 10 Hz to about 500 Hz; and, more preferably, from about 50 Hz to about 250 Hz.

Several possible mechanisms may explain the improved coordination of function across cortical regions which is believed to result from application of electrical stimulation to two or more subdivisions of the patient's intralaminar nuclei. These include changes in global dynamics of a distributed neural network, changes in inhibition or excitation at one or more points in large loops of circuits activated by ILN inputs, and increases in metabolic rates that change the firing rates or other cellular processes. Also, increases in synchrony may promote increased firing rate and increased metabolism or vice versa.

Applicant's copending U.S. patent application Ser. No. 08/985,435, filed Dec. 4, 1997, is hereby incorporated by reference.

In carrying out the present invention, electrical stimulation to at least a portion of the patient's subcortical structures is carried out in response to internally generated movement of the patient. Such movement can be in many forms, including head movement, neck movement, torso movement, and saccadic eye movement.

An advantage of the present invention is that the feedback used to control electrical stimulation of the patient's subcortical structures can also be augmented with non-electrical forms of stimulation. For example, auditory stimulation can be controlled as a function of such feedback with the auditory stimulation being used to activate other portions of the brain.

A particularly preferred embodiment of the present invention involves controlling electrical stimulation in response to saccadic eye movement. Feedback stimulation of specific parameters of oculomotor activity (e.g., saccade onset, intersaccadic interval onset) can be used to optimize intralaminar stimulation by providing a physiologically natural synchronizing pulse for intralaminar targets. Saccadic eye movements are also preferred, because of the widespread nature of the signal in the human brain.

Figure 3:
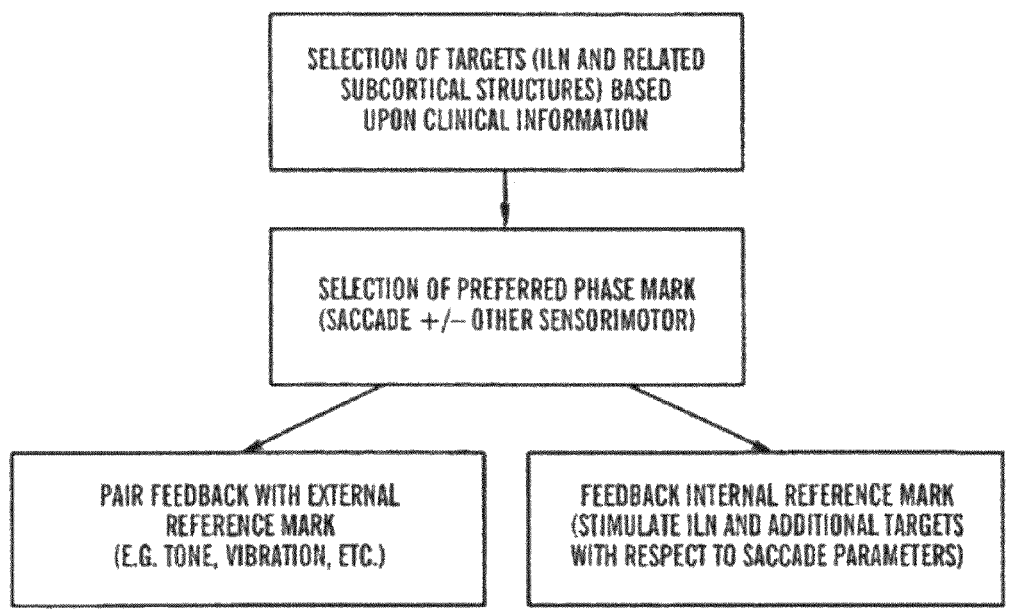
FIG. 3 shows a protocol for implementation of the process of the present invention.

In FIG. 3, the general approach to implementation is shown with initial selection of intralaminar nuclei targets being performed based on clinical considerations. Feedback for intralaminar nuclei stimulation is based on saccadic eye-movement with or without additional pairing of other internally generated repetitive motoric activation (e.g., head turning, pointing, truncal rotation) or external stimulation (e.g., tone or vibratory stimulation). External stimulation pairing is intended to be augmentative. The advantage of pairing the stimulation with sensory stimuli is that coactivation of ascending pathways to primary and secondary sensory cortices that process these signals should allow a wider distribution of common phase marks (or synchronizing signals) to recruit partially impaired cortical regions when combined with activation of the intralaminar targets.

Figure 7:
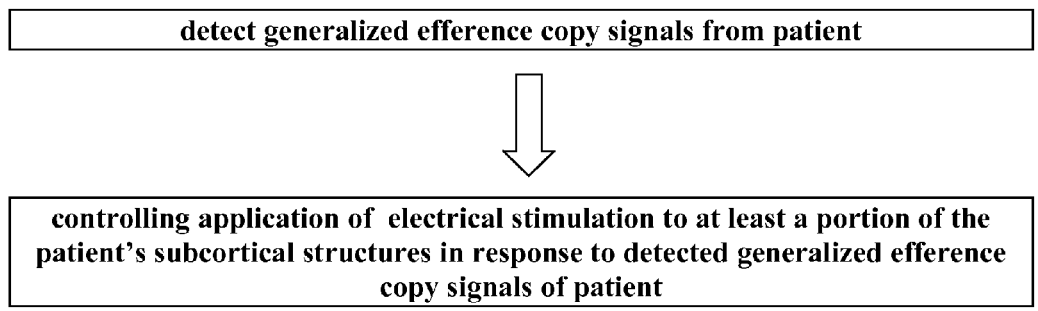
FIG. 7 is a schematic diagram describing the method of treatment of the present invention.

The feedback mechanism of the present invention can be used to control the intensity, frequency, pulse width, and time on/time off of stimulation. Further, the feedback efference copy signal can be used to provide either continuous feedback of endogeneous eye movements requiring indwelling hardware for the continuous monitoring and feedback of the eye movement signal or in a control training setting for rehabilitation where external eye movement monitoring and other monitors or internally generated movement of externally provided phase marks (e.g., tones, vibration etc.) could be paired. Therefore, under one aspect of this invention, the feedback stimulation to the intralaminar nuclei or related targets is akin to a neuronal pacemaker taking advantage of natural brain "beats" or envelopes of activations set by important transients such as the eye movement. In this mode, the feedback is continuous and is used as a brain pacemaker through the intralaminar nuclei and subcortical structures related to saccadic eye movement signals. The other mode is more general, allowing other internal or external phase marks to be coupled to intralaminar nuclei activation for the use of cognitive retraining (see FIG. 7).

Figure 4:
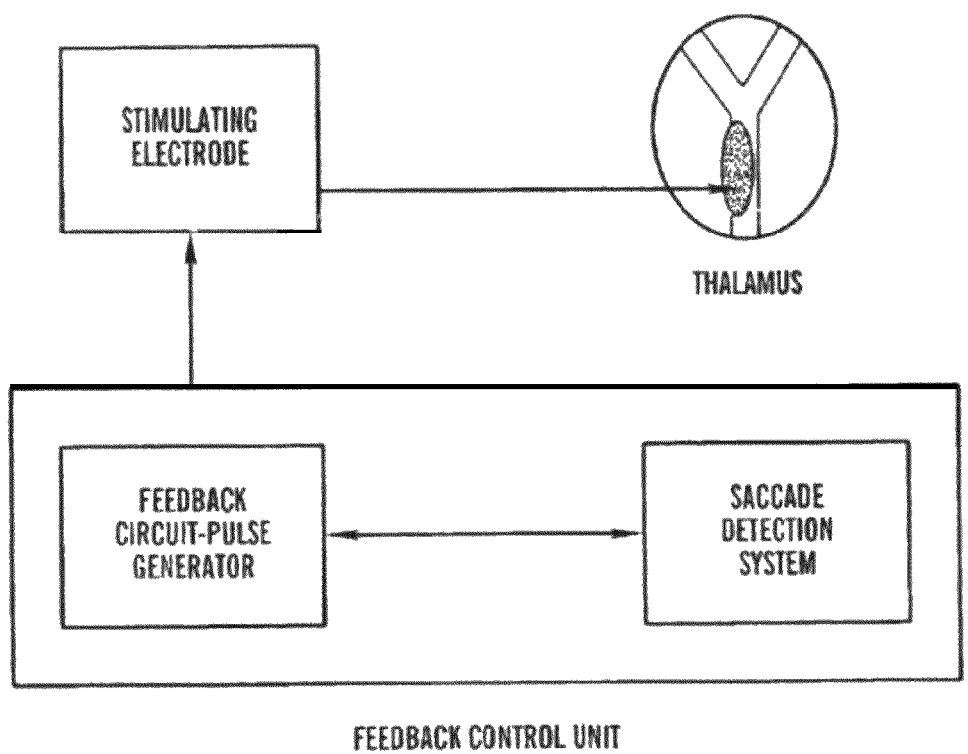
FIG. 4 is a schematic diagram of equipment useful in controlling stimulation of intralaminar nuclei as a function of saccadic eye movement.

FIG. 4 provides a schematic of the hardware required for the implementation of the present invention. As shown in FIG. 4, the stimulating electrode is directed at the thalmus of the patient with activation of the electrode being controlled by a feedback circuit—pulse generator. The feedback pulse generator operates in response to a saccade detection system. A saccade detection system is required to identify saccadic eye-movements and trigger the neurostimulation unit. Several external monitoring systems for saccadic eye movements are presently available and can be adapted for this purpose. Suitable systems include hardware for discrimination of electrooculogram activity or detection using infrared reflection from the pupil or Purkinje fibers (e.g., the ASL E5000 system (Applied Science Laboratories, Bedford, Mass.)). Other methods to detect saccadic eye movements include implanted electrodes to detect electrooculograms, electromyograms, or presaccadic potentials in the electrocephalogram or combinations thereof.

Figure 5:
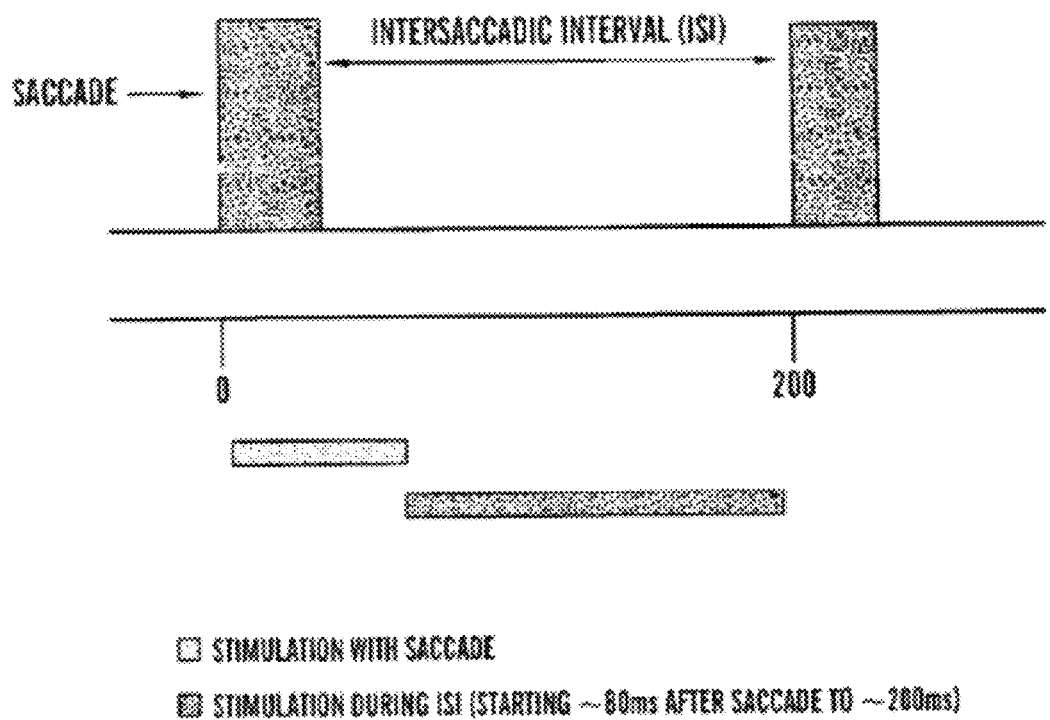
FIG. 5 shows a schematic diagram of pulse sequence time dependence on saccade parameters.

FIG. 5 details the time sequence of saccadic eye movements and indicates two possible times for pulsed activation. In one alternative, stimulating pulses are initiated at the time of the saccadic eye movement. In the alternative embodiments, the stimulating pulse occurs during the intersaccadic interval.

Figure 6A:
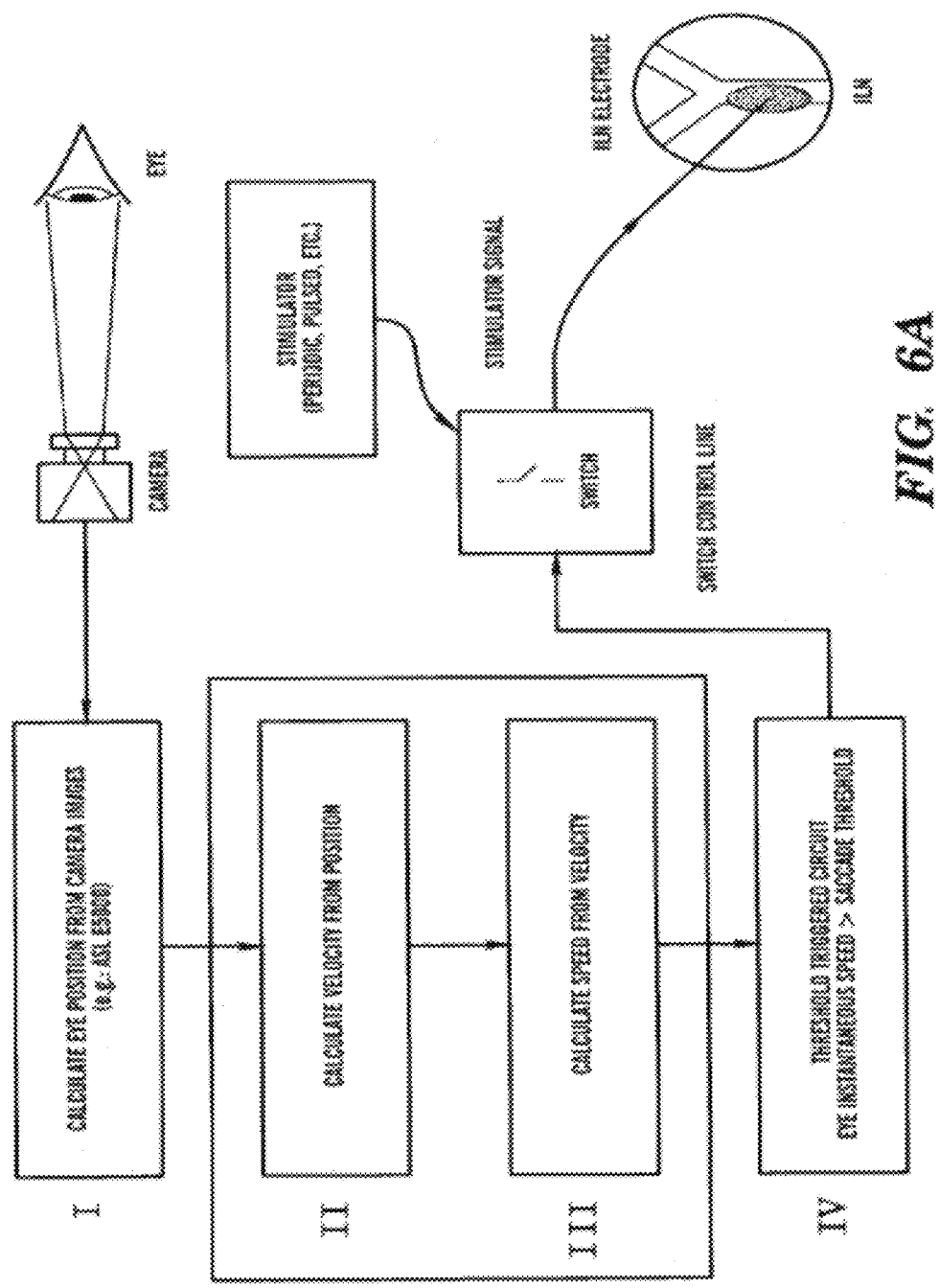
FIG. 6A is a schematic of feedback stimulation from saccadic eye movement.

FIG. 6A shows a more detailed schematic of efference copy synchronization of stimulation based on saccadic eye movements. In Part I, eye position is calculated with an infrared camera (e.g., ASL E5000). Parts II and III calculate the magnitude of the change in eye-position over time. This allows the speed of the eye movement to be identified. In part IV, this speed is compared to a threshold to determine when stimulation should be initiated.

Figure 6B:
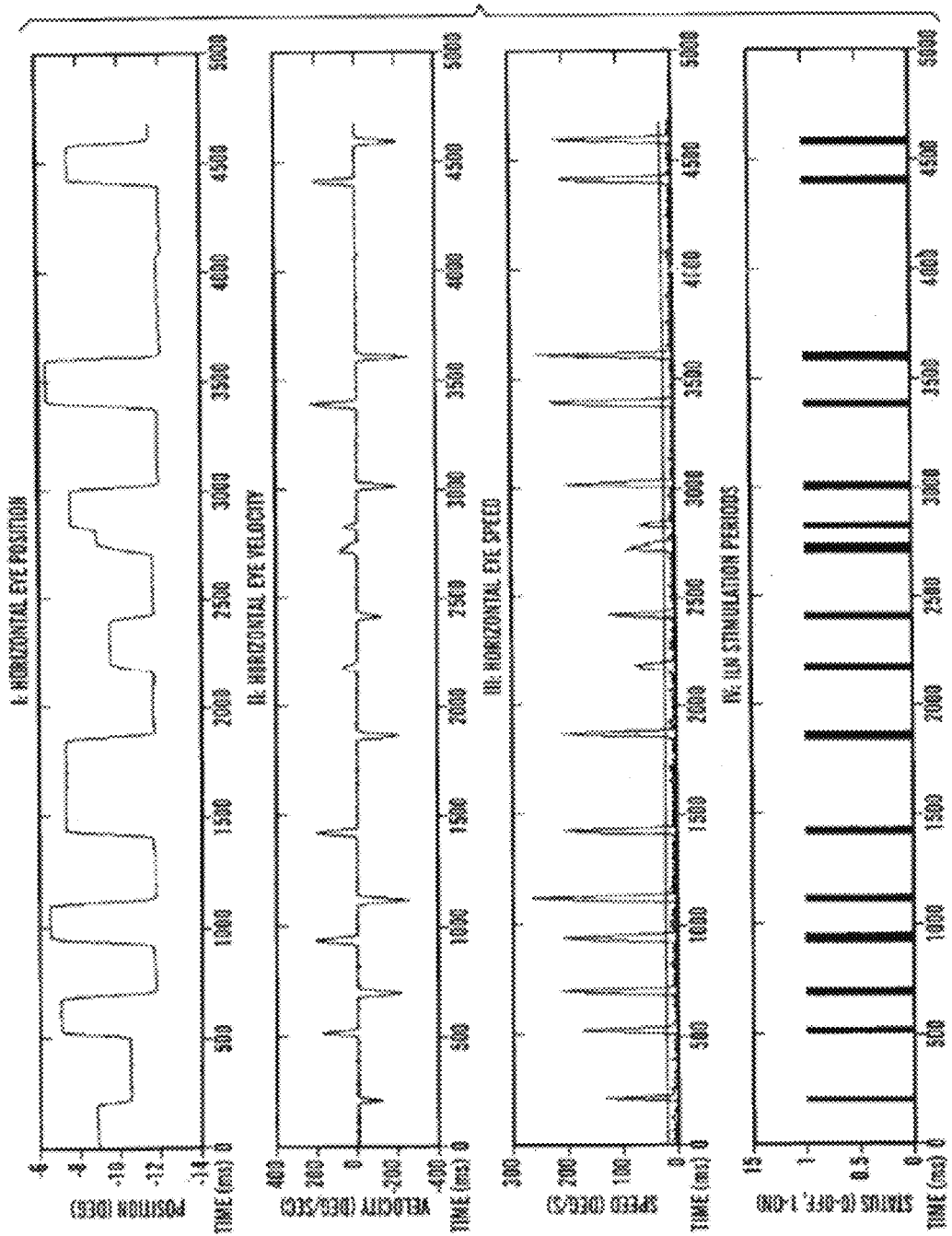
FIG. 6B shows the identification of saccadic eye-movements and feedback pulse control.

FIG. 6B illustrates an example of an eye position signal as it is processed to identify the onset of a saccade and stimulation in response to the saccade. The signals corresponding to each of parts I-IV of FIG. 6A are shown in FIG. 6B. In the first panel (I), horizontal eye positions over time are displayed. In the second panel (II), horizontal velocity has been calculated by the change in horizontal position divided by a 5 millisecond time interval between sampling of positions. In panel III, the absolute value of the velocity (shown in panel II) is plotted along with a threshold for identifying saccadic eye movements (solid line at ~20 degrees/sec). Finally, in panel IV, the starting points of ILN stimulation as triggered at the switch are displayed. Alternative circuit designs would include acceleration triggered circuits or other trigger signals, such as waveforms, if EOG, (electrooculogram-electrical potential change associated with eye movement), EMG (electromyogram-electrical potential changes of the muscles), or EEG saccade related activity is monitored in part IV of FIG. 6A which controls the stimulator.

Eye-movement feedback is further proposed in conjunction with paired activation of other sensory channels (e.g., auditory) or motor gating signals (e.g., head or truncal rotations). Several studies show evidence that intrinsic sequences of brain activation are linked tightly to saccadic eye-movements. In addition, several examples of cognitive improvement are noted in patients who engage in rhythmic head or hand movements, truncal rotation or neck vibration (Vallar). Recent evidence demonstrates that even phasic alerting with pure tones can improve sensory inattention. The intralaminar nuclei-midline system may gate long-range cortico-cortical interactions by computing a generalized efference copy that includes dynamic coordinates for the integration of head, eye, body, and limb positions. The activation of the intralaminar nuclei is proposed to result in the formation of several areas of enhanced neuronal firing rate in both cerebral cortical and striatal structures ("event-holding functions") with an envelope of activation set by the timing of intralaminar nuclei pulses.

The intralaminar nuclei is the preferred target for deep brain stimulation for remediation of cognitive disabilities for several reasons outlined in U.S. patent application Ser. No. 08/985,435, filed Dec. 4, 1997, which is hereby incorporated by reference, including, importantly, the economy of one stimulation site activating several regionally selective cortical and subcortical targets to modulate their neuronal firing rates, metabolism, or behavioral expression of the networks they comprise. In patients who may otherwise be good candidates for this therapy, direct injury to the intralaminar nuclei or surrounding thalamic or white matter tissue may prevent the application of the described method. The present invention has two purposes. One is to improve treatment by introducing feedback stimulation of the natural physiological signals computed in the intralaminar nuclei and passed to the cortical and subcortical targets. The other is to take advantage of secondary targets for deep brain stimulation using the feedback mechanism to provide a synchronizing pulse, particularly, or preferably in situations where the optimal intralaminar nuclei targets are not available.

An example of a practical situation where intralaminar nuclei stimulation, as described in U.S. patent application Ser. No. 08/985,435, filed Dec. 4, 1997, which is hereby incorporated by reference, would be prevented from having an optimal therapeutic effect is the patient described by De La Sayette et al., "Infarction in the Territory of the Right Choroidal Artery and Minor Hemisphere Syndrome: Case Report and Brain Glucose Utilization Study," Rev. Neurol. 151(1): 24-35 (1995), which is hereby incorporated by reference, with an infarction of the right anterior choriodal artery resulting in a "thalamic exclusion" syndrome with a severe metabolic deficit that persisted months after the injury. In this patient, vestibular stimulation demonstrated that residual functional activity could be recovered from the severely damaged right hemisphere. Using the method disclosed here, it is proposed that paired feedback stimulation of the left intralaminar nuclei (central lateral or parafasicularis) and the right caudate nucleus (which demonstrated residual metabolism) would support a tonic reactivation of the functionally impaired right hemisphere. Excepting the right mesencephalic reticular formation, other right hemisphere targets in this patient were either severely damaged (globus pallidus) or anatomically disconnected (all thalamic targets—intralaminar nuclei and others).

Thus, combined use of feedback of the oculomotor signal to a deep brain stimulator can optimize the stimulation of the intralaminar nuclei-midline thalamic structures in cases where the preferred targets may not be available due to direct structural injuries or to indirect obstruction to the preferred implementation (e.g., direct thalamic injury, loss of white matter connection, neoplastic change in path of electrode, etc). Feedback stimulation of part of the intralaminar nuclei and additional related subcortical structures receiving direct intralaminar nuclei innervation such as the caudate, putamen, or responding to saccadic eye movements such as globus pallidus interna, dorsal median or pulvinar thalamic nuclei or pretectum, mesencephalic reticular formation or superior colliculus could in this way be combined with intralaminar nuclei targets. See Leigh et al., *The Neurology of Eye Movement* (Oxford Univ. Press 1999), which is hereby incorporated by reference.

The activation of specific intralaminar targets (i.e. central lateral, paracentralis, and the centromedian-parafascicularis complex) driven by continuous parameters of the patient's endogenous eye movements (i.e. saccades, microsaccades) can also be used to optimize intralaminar nuclei stimulation for the purpose of remediating cognitive disability. Such activation may be based on voluntary eye movements in training sequences as well as continuous feedback of endogenous eye movements. Neuronal populations mediating voluntary versus learning automatic saccadic sequences (e.g., main sequence of saccades (Hayhoe et al. "Task Constraints in Visual Working Memory," *Vision Res.* 38(1):125-37 (1998) ("Hayhoe"), which is hereby incorporated by reference), or reading (see Reichle et al., "Toward a Model of Eye Movement Control in Reading," *Psychol. Rev.* 105(1):125-57 (1998), which is hereby incorporated by reference), and efficacy of feedback would likely vary on basis of underlying brain injury. Using the feedback circuit to the neurostimulation unit in conjunction with voluntary saccades, training paradigms may be used for intervals to selectively pair eye-movement feedback with visuomotor activity (Hayhoe), perceptual retraining (Robertson et al., "Prospects for the Rehabilitation of Unilateral Neglect," in Robertson et al., *Unilateral Neglect: Clinical and Experimental Studies* (1993), which is hereby incorporated by reference), or memory formation retrieval (Kinsbourne, "Eye and Head Turning Indicates Cerebral Lateralization," *Science* 176:539-41 (1972) and Purpura et al., "The Thaliamic Intralaminar Nuclei: A Role in Visual Awareness, *Neurosci pp.* 8-15 (1997) ("Purpura"), which are hereby incorporated by reference).

One theory of the present invention is that intralaminar nuclei activation of multiple cortical and subcortical regions is generated as the result of computing a generalized efference copy signal. By definition, an efference copy is an internal copy of a motor innervation (von Holst et al., "Das Reafferenzprinzip. Wechselwirkungen zwischen Zentral Nerven System und Peripheries," *Naturwissenschaften* 37:464-76 (1950) and Bridgeman, "A Review of the Role of Efference Copy in Sensory and Oculomotor Control System," *Ann. Biomed. Eng.* 23:409-22 (1995), which are hereby incorporated by reference) and, as such, is the control signal used by a system to organize its behavior. One example of such signalling is the unique reporting of central lateral nucleus intralaminar neurons of oculomotor function (Schlag-Rey et al., "Visumotor Functions of Central Thalamus in Monkey. I. Unit Activity Related to Spontaneous Eye Movements," *J. Neurophysiol.* 40:1149-74 (1984) and Purpura, which are hereby incorporated by reference). Other types of efference copy are also associated with the intralaminar nuclei such as rhythmic motor behavior and verbal fluency (Mennemeier et al., "Tapping, Talking, and the Thalamus: Possible Influence of the Intralaminar Nuclei on Basal Ganglia Function," *Neuropsych.* 35(2):183-93 (1997), which is hereby incorporated by reference). Intralaminar nuclei activations are thought to activate and synchronize several parallel thalamocortical basal ganglia loops (Gronewegen). In the present invention, known vestibular, oculomotor, auditory, somatosensory, and other afferents to the intralaminar nuclei are combined and translated as generalized efference copy to selectively activate functional collections of cortical and striatal targets. Feedback of internally generated movements (eye movements, truncal, neck, limb, etc.) is proposed to enhance the functional recovery of impaired cerebral regions by deep brain stimulation of the intralaminar nuclei by providing a physiological natural synchronizing pulse to these regions and their target structures. By enhancing the internal efference copy signal and rechanneling these signals to other brain structures prepared to accept the activation, reintegration of impaired (but potentially functional) networks will be promoted.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A cognitive function improving apparatus comprising: (i) means for applying electrical stimulation to at least a portion of a patient's subcortical structures involved in the control of generalized efference copy signals; (ii) means for detecting generalized efference copy signals of the patient; and (iii) means for controlling the applied electrical stimulation in response to detected generalized efference copy signals of the patient.

2. The cognitive function improving apparatus according to claim 1, wherein the means for controlling the applied electrical stimulation is capable of providing continuous, intermittent or periodic stimulation.

3. The cognitive function improving apparatus according to claim 1, which is capable of patient biofeedback.

4. The cognitive function improving apparatus according to claim 1, wherein the means for controlling the applied electrical stimulation in response to detected generalized efference copy signals of the patient is capable of controlling at least one of the parameters of intensity, frequency, pulse width and the time on and time off of the applied electrical stimulation.

5. The cognitive function improving apparatus according to claim 4, wherein the electrode is capable of delivering pharmacological agents to a patient's subcortical structures.

6. The cognitive function improving apparatus according to claim 5, wherein the electrode has microcannulae suitable for delivering pharmacological agents to a patient's subcortical structures.

7. The cognitive function improving apparatus according to claim 1, wherein the means for controlling the applied electrical stimulation comprises a pulse generator.

8. The cognitive function improving apparatus according to claim 7, wherein the pulse generator is capable of generating voltage wave trains in sine, square, spike, rectangular, triangular or ramp form.

9. The cognitive function improving apparatus according to claim 1, wherein the means for applying electrical stimulation to at least a portion of an individual's subcortical structures involved in the control of generalized efference copy signals comprises an electrode capable of delivering an electrical signal to a patient's intralaminar nuclei.

10. The cognitive function improving apparatus according to claim 9, wherein the electrode is capable of applying electrical stimulation at a frequency of from 1 Hz to 1 kHz.

11. The cognitive function improving apparatus according to claim 10, wherein the electrode is capable of applying electrical stimulation at a frequency of from 10 Hz to 500 Hz.

12. The cognitive function improving apparatus according to claim 11, wherein the electrode is capable of applying electrical stimulation at a frequency of from 50 Hz to 250 Hz.

13. The cognitive function improving apparatus according to claim 9, wherein the electrode is capable of delivering an electrical signal to at least a selected subdivision of the patient's intralaminar nuclei, which subdivision modulates a specific cognitive function.

14. The cognitive function improving apparatus according to claim 13, wherein the electrode is capable of delivering an electrical signal only to the selected subdivision.

15. The cognitive function improving apparatus according to claim 9, wherein the electrode is an implantable multipolar electrode comprising an implantable pulse generator that is a radiofrequency controlled device operatable by an external transmitter.

16. The cognitive function improving apparatus according to claim 9, wherein the implantable multipolar electrode contacts allow for adjustment of frequency, amplitude and pulse width.

17. The cognitive function improving apparatus according to claim 16, wherein the implantable multipolar electrode contacts allow for adjustment of frequency within the range of about 2-200 Hz, the adjustment of amplitude within the range of about 0.1-10 Volts and the adjustment of pulse width within the range of about 50-500 microseconds.

18. The cognitive function improving apparatus according to claim 1, wherein the means for applying electrical stimulation to at least a portion of a patient's subcortical structures involved in the control of generalized efference copy signals is capable of applying electrical stimulation to two or more subdivisions of a patient's intralaminar nuclei which modulate separate cortical regions.

19. The cognitive function improving apparatus according to claim 18, which is capable of applying electrical stimulation to two or more subdivisions of a patient's intralaminar nuclei which modulate separate cortical regions in a synchronized manner.

20. The cognitive function improving apparatus according to claim 19, further comprising means capable of identifying regional or intrahemispheric changes in brain waves in response to the applied electrical stimulation to two or more subdivisions of a patient's intralaminar nuclei.

21. The cognitive function improving apparatus according to claim 1, further comprising means for non-electrical stimulation of a patient.

22. The cognitive function improving apparatus according to claim 21, wherein the means for non-electrical stimulation of a patient is a means capable of auditory stimulation of a patient.

23. An apparatus for improving coordination of function across cortical regions in a patient comprising the cognitive function improving apparatus as defined in claim 1, wherein: (i) said means for applying electrical stimulation comprises means for applying electrical stimulation to two or more subdivisions of a patient's subcortical structures involved in the generation and control of generalized efference copy signals, wherein the two or more subdivisions of a patient's subcortical structures modulate separate cortical regions.

24. The apparatus according to claim 23, wherein the means for applying electrical stimulation to two or more subdivisions of a patient's subcortical structures is capable of applying electrical stimulation to two or more subdivisions of the patient's intralaminar nuclei.

25. The apparatus according to claim 24, wherein the means for applying electrical stimulation to two or more subdivisions of a patient's subcortical structures is capable of applying electrical stimulation to two or more subdivisions of a patient's intralaminar nuclei in a synchronized manner.

26. The apparatus according to claim 23, wherein the means for controlling the applied electrical stimulation is capable of providing periodic stimulation.

27. A chronic pain and/or generalized seizure treatment apparatus comprising the cognitive function improving apparatus as defined in claim 1, wherein: (i) said means for applying electrical stimulation comprises means for applying electrical stimulation to at least a portion of a patient's subcortical structures involved in the generation and control of generalized efference copy signals under conditions effective to treat the patient's chronic pain and/or generalized seizures.

28. The apparatus according to claim 27, wherein the means for applying electrical stimulation to at least a portion of a patient's subcortical structures involved in the generation and control of generalized efference copy signals comprises an electrode capable of delivering an electrical signal to the patient's intralaminar nuclei.

29. The apparatus according to claim 28, wherein the electrode is capable of delivering an electrical signal to the patient's paralamellar regions.

30. The apparatus according to claim 28, wherein the electrode is capable of delivering an electrical signal only to said portion of the patient's intralaminar nuclei involved in the generation and control of generalized efference copy signals.

31. The apparatus according to any of claim 27, wherein the means for controlling the applied electrical stimulation is capable of providing continuous, intermittent or periodic stimulation.

32. The apparatus according to claim 27, wherein the means for detecting generalized efference copy signals of the patient comprises means for monitoring specific regional or intrahemispheric changes in distribution of power or coherence within a frequency spectrum.

33. The apparatus according to claim 27, wherein the means for detecting generalized efference copy signals of the patient comprises indwelling hardware for monitoring endogeneous eye movement.

34. A brain injury treatment apparatus comprising the cognitive function improving apparatus as defined in claim 1, wherein: (i) said means for applying electrical stimulation comprises means for applying electrical stimulation to at least a portion of a patient's subcortical structures involved in the generation and control of generalized efference copy signals under conditions effective to treat the patient's brain injury.

35. A post-encephalitic Parkinsonism treatment apparatus comprising the cognitive function improving apparatus as defined in claim 1, wherein: (i) said means for applying electrical stimulation comprises means for applying electrical stimulation to at least a portion of a patient's subcortical structures involved in the generation and control of generalized efference copy signals under conditions effective to treat the patient's post-encephalitic Parkinsonism.

36. An oculogyric crises treatment apparatus comprising the cognitive function improving apparatus as defined in claim 1, wherein: (i) said means for applying electrical stimulation comprises means for applying electrical stimulation to at least a portion of a patient's subcortical structures involved in the generation and control of generalized efference copy signals under conditions effective to treat the patient's oculogyric crises.

37. The apparatus according to claim 1, wherein said means for detecting generalized efference copy signals detects saccadic eye movement.

38. The apparatus according to claim 37, wherein the means for detecting saccadic eye movement comprises:
(i) hardware capable of discrimination of electroculogram activity or detection using infrared reflection from the pupil or Purkinje fibres; or
(ii) electrodes suitable for implantation and, when so implanted, capable of detection of electrooculograms, electromyograms, presaccadic potentials in the electrocephalogram or combinations thereof.

* * * * *